(12) United States Patent
Canfield et al.

(10) Patent No.: US 6,492,152 B1
(45) Date of Patent: Dec. 10, 2002

(54) CORE 1 β3-GALACTOSYL TRANSFERASES AND METHODS OF USE THEREOF

(75) Inventors: William M. Canfield, Oklahoma City; Richard D. Cummings, Edmond; Tongzhong Ju, Oklahoma City, all of OK (US)

(73) Assignee: The Board of Regents of the University of Oklahoma

( * ) Notice: Subject to any disclaimer, the term of this patent is extended or adjusted under 35 U.S.C. 154(b) by 0 days.

(21) Appl. No.: 09/464,035

(22) Filed: Dec. 15, 1999

Related U.S. Application Data

(63) Continuation-in-part of application No. 09/334,013, filed on Jun. 15, 1999.

(51) Int. Cl.⁷ .............................. C12N 9/08; C12N 1/20; C12N 15/00; C12P 21/06

(52) U.S. Cl. ...................... 435/193; 435/69.1; 435/183; 435/190; 435/200; 435/252.3; 435/320.1; 536/23.2

(58) Field of Search ................................ 435/69.1, 183, 435/200, 252.3, 320.1, 193, 194, 350, 68.1, 325; 536/23.2

(56) References Cited

U.S. PATENT DOCUMENTS

| | | | |
|---|---|---|---|
| 5,047,335 A | 9/1991 | Paulson et al. | 435/69.1 |
| 5,180,674 A | 1/1993 | Roth | 435/288 |
| 5,821,329 A | 10/1998 | Lobl et al. | 530/317 |
| 5,827,817 A | 10/1998 | Larsen et al. | 514/2 |
| 5,874,261 A | 2/1999 | Roth | 435/97 |

FOREIGN PATENT DOCUMENTS

| | | |
|---|---|---|
| EP | 0577580 | 1/1994 |
| EP | 0679716 | 11/1995 |
| WO | 9706176 | 2/1997 |
| WO | 9951185 | 10/1999 |
| WO | 9965712 | 12/1999 |

OTHER PUBLICATIONS

Brockhausen et al., 1992, Biochem. Cell Biol. vol. 70:99–108.*
Amado et al, A Family of Human β3–Galactosyltransferase (May 22, 1998) J. Biol. Chem., vol. 273, No. 21, pp. 12770–12778.
Atushi et al, Detection of protein–protein interactions in the nervous system using the two–hybrid system, Trends in Neuroscience (1996) 19:261–266.
Bierhuizen et al., "Expression Cloning of a cDNA encoding UDP–GlcNAc:Galβ1–3–GalNAc–R (GlcNAc to GalNAc) β1–6GlcNAc transferase by Gene Transfer Into CHO Cells Expressing Polyoma Large Tumor Antigen," *Proc. Natl. Acad. Sci. USA*, 89:9326–9330, Oct. 1992.

Brockhausen et al., Control of O–glycan synthesis: specificity and inhibition of O–glycan core 1 UDP–galactose: N–acetylgalactosamine–αR β3–galactosyltransferase from rat liver (1992), Biochem. Cell Biol., vol. 70, pp. 99–108.
Cheng et al., Mucin Biosynthesis (1982) J. Biol. Chem., vol. 257, No. 11. pp. 6251–6258.
Copy of PCT International Search Report for PCT/US99/13455, Cummings et al., Jun. 15, 1999.
Delhom et al. Synthesis of Sulfated Bioactive Peptides Using Immobilized Arylsulfotransferase from Eubacterium sp. *Biotechnol. Lett.* May 1996, vol. 18, No. 5, pp. 609–614, entire document.
Gronovsky et al., UDPgalactose:glycoprotein–N– acetyl–D–galactosamine 3–β–D–galactosyltransferase activity synthesizing O–glycan core 1 is controlled by the Amino acid sequence and glycosylation of glyco . . . (1994) Eur. J. Biochem., vol. 221, pp. 1039–1046.
Meier et al., "The ELAM LIgand Fucosyltransferase, ELFT, Directs E–Selectin Binding to a Secreted Scaffold Protein: A Method to Produce and Purify Large Quantities of Specific Carbohydrate Structures," *Chemical Abstracts*, XP–002124245, 119(17), 20/25/93.
Moore et al., "The P–Selectin Glycoprotein Ligand From Human Neutrophils Displays Sialylated, Fucosylated, O–Linked Poly–N–Acetyllactosamine," *The Journal of Biological Chemistry*, 269(37):23318–23327, 1994.
Pouyani et al. PSGL–1 Recvognition of P–Selectin is Controlled by a Tyrosine Sulfation Consensus at the PSGL–1 Amino Terminus. *Cell*. Oct. 20, 1995, vol. 83, No. 2, pp. 333–343, entire document.
Sako et al., A sulfated Peptide Segment at the Amino Terminus of PSGL–1 is Critical for P–Selectin Binding. *Cell*. Oct. 20, 1995, vol. 83, No. 2, pp. 323–331, entire document.
Seitz et al., "Chemoenzymatic Solution– and Solid–Phase Synthesos of O–Glycopeptides of the Mucin Domain of MAdCAM–1, A General Route to O–LacNAc, O–Sialyl–LacNAc and O–Sialyl–Lewis–X Peptides," *J. Am. Chem. Soc.*, 119:8766–8776, 1997.

(List continued on next page.)

*Primary Examiner*—Rebecca E. Prouty
*Assistant Examiner*—Manjunath N. Rao
(74) *Attorney, Agent, or Firm*—Dunlap, Codding, & Rodgers, P.C.

(57) ABSTRACT

Core 1 β3-galactosyl transferases and nucleic acids encoding the core 1 β3-galactosyl transferases are described. The enzymes and the nucleic acids encoding said enzymes have been identified in human, rat, mouse *D. melanogaster* and *C. elegans*. The polypeptides exhibit a wide range of homologies. The polynucleotides can be used to transform or transfect host cells for producing substantially pure forms of the enzyme, or for use in an expression system for post-translational core 1 O-linked glycosylation of proteins or peptides produced within the expression system. The enzymes can be used to galactosylate, via a β3-linkage, an N-acetylgalactosamine linked to a serine, threonine or other O-linking amino acid on peptides or proteins requiring O-linked glycosylation.

10 Claims, 8 Drawing Sheets-

OTHER PUBLICATIONS

Sueyoshi et al., "Expression of Distinct Fucosylated Oligosaccharides and Carbohydrate–Mediated Adhesion Efficiency Directed by Two Different α–1,3–fucosyltransferases," *The Journal of Biological Chemistry*, 269(51):32342–32350, 1994.

Wilkins et al. Structures of the O–Glycans on P–Seletin Glycoprotein Ligand–1 from HL–60 Cells. *Journal Biol. Chem.* Aug. 2, 1996, vol. 271, No. 31, pp. 18732–18742, entire document.

Wünsch et al. Synthesis of Cholecystokinin–Related Peptides and Their Biological Properties. *Biol. Chem. Hoppe–Seylor.* Apr. 1989, vol. 370, pp. 317–321, entire document.

Yamamoto et al. Chemoenzymatic Synthesis of a Novel Glycopeptide Using a Microbial Endoglycosidase. *Caro. Res.* Jan. 9, 1998, vol. 305, No. 3–4, pp. 415–422, entire document.

Adams et al., "The Genome Sequence of Drosophia Melanogaster," (Mar. 24, 2000), *Science*, 287:2185–2195.

Amado et al., "Identification and characterization of large galactosyltransferase gene families: galactosyltransferases for all functions," (Dec. 6, 1999) *Biochim. Biophs. Acta*, 1473: 35–53.

Brockhausen et al., "Enzymatic basic for sialyl–Tn expression in human colon cancer cells," (1998) *Glycoconjugate J.*, 15:5959–603.

Ju et al., "Purification, Cloning and Expression of Core 1 beta3–Galactosyltransferase," (Oct. 1999) *Glycobiology*, vol. 9 (whole document):86.

Leppänen et al., "A Novel Glycosulfopeptide Binds to P–selectin and Inhibits Leukocyte Adhesion to P–selectin," (1999) *J. Biol. Chem.*, 274:24838–24848.

Lopez et al., "O–Glycosylation opential of lepidopteran insect line," (1999) Biochimica et. Biophysica Acta, vol. 1427:49–61.

Schachter et al., "The Biosynthesis of Serine (Threonine)–N–Actylgalactosamine–Linked Carbohydrate Moieties," (1992) In. *Glycoconjugates Composition, Structure & Functioni*, pp. 263–332.

Schachter et al., "Sialic Acids," (Sep. 10, 1971) *J. Biol. Chem.*, 246:5321–5328.

Sherwood et al., "Stable Expression of a cDNA Encoding a Human Beta 1→3Galactosyltransferase Responsible for Lacto–Series Type 1 Core Chain Synthesis in Non–Expressing Cells: Variation in the Nature of Cell Surface Antigens Expressed," (Oct. 1, 1992) J. Cellular Biochem. 50:165–177.

Thurnher et al., "T Cell Clones with normal or defective O–galactosylation from a patient with permanent mixed field polyagglutinability," (1992) *Eur. J. Immunol.*, 22;1835–1842.

Wilson et al., "2.2Mb of contiguous nucleotide sequence from chromosome III of *C. elegans*," (Mar. 3, 1994) *Nature*, 368:32–38.

Zeng et al., "Complete enzymic synthesis of the mucin–type sialyl Lewis x epitode, involved in the interaction between PSGL–1 and P–selectin," (1999) *Glycoconjugate J.*, 16:487–497.

Kleen & Burger, Molecular of Cell Biology of Glylosyl Transferases, Biochime & Biophys. Acta., (1993), vol. 1154: 283–325.

* cited by examiner

Core1 β3 Gal-transferase Purification Table

| | Step | Protein | | | Core1 β3 GalT Activity | | | Yeild (%) | Purification -fold |
|---|---|---|---|---|---|---|---|---|---|
| | | Volume (ml) | Conc. (Mg/ml) | Total (Mg) | Activity ◆(units/ml) | Specific Activity (units/mg) | Total (units) | | |
| 1 | ▲ Post Nuclear Supernatant | 1460 | 34.6 | 50,516 | 102 | 2.9 | 148,920 | 100 | 1.0 |
| 2 | Solubilized Membrane | 1000 | 13.8 | 13,800 | 136 | 9.8 | 136,000 | 91.3 | 3.4 |
| 3 | Sp-Sepharose Pool◆ | 300 | 4.2 | 1,260 | 142 | 33.8 | 42,600 | 28.6 | 11.7 |
| 4 | Asialo-BSM UltraLink™ Pool | 9 | 0.009 | 0.081 | 1,461 | 162,333 | 13,149 | 8.8 | 55,862 |
| 5 | Superose 12 Pool | 4 | 0.015 | 0.060 | 3,090 | 206,000 | 12,360 | 8.3 | 71,034 |

◆ Unit: nmol/hr
▲ Rat Liver: ~500 g
● Using 1 M NaCl in 25 mM MES pH 6.5, 0.1% Triton Figure 1. Purification of Core 1 β3Gal-transferase

TACAGCTTTGATTTTATAAACATCCTGCTAATTTTTGTTCTTACAGAAATACACTTTCGGG

TTCTTTTATGTTCTCAGCTATTTAGTATTTTGTTGGGAGAAAAAGGTTGACACCCAGCCTA
 F  L  C  S  Q  L  F  S  I  L  L  G  E  K  V  D  T  Q  P

AAGGACAAATGAACTTCAATGCAGATTCTAGCCAACATAAAGATGAGAACACAGACATTG
 E  G  Q  M  N  F  N  A  D  S  S  Q  H  K  D  E  N  T  D  I

TAGAGAAAAAGGCCAAACGTCAAAGCTACTTGGGCCCAGCGTTGTAACAAAGTGTTGT
 L  E  K  K  A  K  H  V  K  A  T  W  A  Q  R  C  N  K  V  L

GAGATCAACTATACTGGAAAAACAATTAAAGCTTTTCAGTATGTTCATGAACATTATTTAG
 R  D  Q  L  Y  W  K  T  I  K  A  F  Q  Y  V  H  E  H  Y  L

GGTGGCTTCTTTCAAAATACGACCCTGAAGAACCCATTTACTTTGGGAGAAGATTTAAGC
 R  W  L  L  S  K  Y  D  P  E  E  P  I  Y  F  G  R  R  F  K

TGAAAAGATTGTTGATGCATTTAAAACAGACAAGTGTACACATAGTTCCTCCATTGAAG
 L  K  R  F  V  D  A  F  K  T  D  K  C  T  H  S  S  S  I  E

CCATTGGAAAAGAAAACTTTCATCCCTTTGTGCCAGAACACCATTTAATTAAAGGTTATC
 T  I  G  K  E  T  F  H  P  F  V  P  E  H  H  L  I  K  G  Y

GCTGCCTCTGATCTTGCAGTTTCTTTTCACTATGTTGATTCTACAACCATGTATGAGTTAG
 C  C  S  D  L  A  V  S  F  H  Y  V  D  S  T  T  M  Y  E  L

CTGAACGTATACTAAAGGAAATTAGTCAAGCAAACAAAAATGAAGATACAAAAGTGAAGT
 P  E  R  I  L  K  E  I  S  Q  A  N  K  N  E  D  T  K  V  K

AAAAAGGACTTTCTGCATTTCTGACATAGAACACTGGAATCCCAGTGAGGAATTCTAAGTG
TGAAGTGTGTTAAAATGTGTTTGATACAGTAATATAAATATGTCTATATATATGAGG
TTTTCTGACCATCTGTGTTATTGTCACTGAGAAACTAAAATAGTAAATTTACTAAAACTA
ATATTGTTGCTCAGTGTGTTGTTAATATAGCTCAAGAATTGAGTTTATATTTGCAGTATGCT
GTGATTATTTATAATTGGTAGTATTCTTCCAGAAGAAGCTAAAATAAGACTGGCACTTA

Figure 3A

```
AAATGGCCTCTAAATCCTGGCTGAATTTTTAACCTTCCTCTGTGATCAGCAATAGGAT      120
     M  A  S  K  S  W  L  N  F  L  T  F  L  C  G  S  A  I  G      19
ATGTTCTTCATAATGATCCTCATGCAAGGCATTCAGATGATAATGGACAGAATCATCTAG    240
 N  V  L  H  N  D  P  H  A  R  H  S  D  D  N  G  Q  N  H  L     59
CTGAAAACCTCTATCAGAAGTTAGAATTCTTTGCTGGTTATGACCGGCCCTCAAAACC      360
  A  E  N  L  Y  Q  K  V  R  I  L  C  W  V  M  T  G  P  Q  N    99
TTATGAGTTCAGAAGAAAATAAAGACTTCCCTGCTGTGGGACTGAAAACCAAAGAAGGCA    480
 F  M  S  S  E  E  N  K  D  F  P  A  V  G  L  K  T  K  E  G     139
AAGATGCTGATTGGTTTTTGAAAGCAGATGATGACACGTATGTCATACTAGACAATTTGA    600
 E  D  A  D  W  F  L  K  A  D  D  D  T  Y  V  I  L  D  N  L     179
CTTATGTAAAGCAGGGCTACATGAGTGGAGGAGGCAGGATATGTAAGAAGCAGGAGATTCCAGAGATA   720
 P  Y  V  K  Q  G  Y  M  S  G  G  A  G  Y  V  L  S  K  E  A     219
ACTTAGCACTGGGGAGATGCATGGAATTATGAATGTAGAAGCAGGAGATTCCAGAGATA    840
 D  L  A  L  G  R  C  M  E  I  M  N  V  E  A  G  D  S  R  D     259
TACCTAGAACGTTTTGGTACTGAATTACATCTTCGTCCATATGGTTATTTATACAGATATCAACCTTAC   960
 L  P  R  T  F  W  Y  W  N  Y  N  Y  Y  P  P  V  E  G  P  G     299
AATACCCTCGTTTATCATCTTCGTCCATATGGTTATTTATACAGATATCAACCTTAC      1080
 E  Y  L  V  Y  H  L  R  P  Y  G  Y  L  Y  R  Y  Q  P  T  L     339
TAGGAAATCCTTGAAAGAAAATCATGAATGAACAAAGGTAATATGTCTAGCACTGCACTG    1200
 L  G  N  P  *                                                  363
AACATTCCTTATAGAAACCTTTCACATGAATGACTATAAACTGAAGCTTTAAATGAGCTG    1320
AACTTGTGTTTTTTAAATGGTGGCCAGTGGCCAGGAACTAGAGAACTAGAAAAGAGATTTTGTTGCCTG  1440
CACTGCACCATGTTAGTAATAAACAGATCTGCCTTAAAGAAAAGAAAATTTTAGAAAGAA    1560
ATAAATGATACCCCCTACCACCACACACACAGTTTTGTCTAATGAAAAATGTTGCT        1680
CCCTGAAGTGCATTAATAAACCACACTTTAAAATTAAAAAAAAAAAAAAAAAA            1794
```

Figure 3B

Figure 4A:
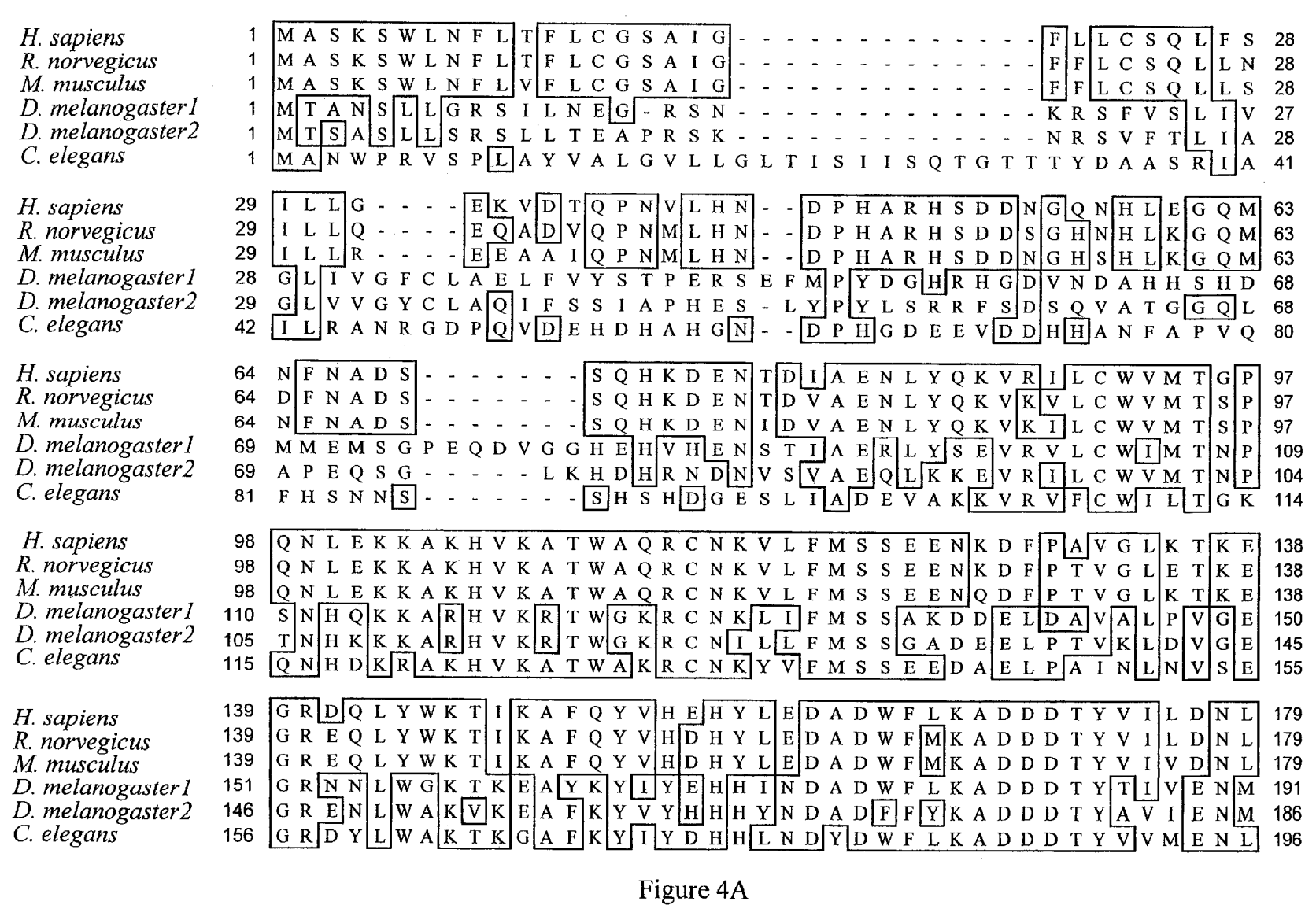

| | | | | |
|---|---|---|---|---|
| H. sapiens | 1 | MASKSWLNFLT | FLCGSAIG | --------- | FLLCSQLFS | 28 |
| R. norvegicus | 1 | MASKSWLNFLT | FLCGSAIG | --------- | FFLCSQLLN | 28 |
| M. musculus | 1 | MASKSWLNFLV | FLCGSAIG | --------- | FFLCSQLLS | 28 |
| D. melanogaster1 | 1 | MTANSLLGRSILNEG-RSN | --------- | KRSFVSLIV | 27 |
| D. melanogaster2 | 1 | MTSASLLSRLLTEAPRSK- | --------- | NRSVFTLIA | 28 |
| C. elegans | 1 | MANWPRVSPLAYVALGVLLGLTISIISQTGTTTYDAASRLA | 41 |

CORE 1 β3-GALACTOSYL TRANSFERASES AND METHODS OF USE THEREOF

CROSS-REFERENCE TO RELATED APPLICATIONS

The present application is a continuation-in-part of copending application U.S. Ser. No. 09/334,013, entitled "SYNTHETIC GLYCOSULFOPEPTIDES AND METHODS OF SYNTHESIS THEREOF", filed Jun. 15, 1999, the Specification of which is hereby incorporated herein by reference in its entirety.

BACKGROUND

The present invention is related to core 1 β3-galactosyl transferases, polynucleotides which encode said core 1 β3-galactosyl transferases and methods of use thereof.

The core 1 O-linked glycan structure, consisting of galactose linked β3 to N-acetylgalactosamine linked to a threonine or serine on a protein, peptide or polypeptide, is a critical intermediate in the biosynthesis of most extended O-linked glycans (*Glycoproteins and Human Disease* (Brockhausen, I., and Kuhns, W., eds), (1997), pp. 13–31, R.G. Landes Company, Austin). The core 1 structure is found on a number of mucins and adhesion molecules. Core 1 β3-galactosyl transferase is the only enzyme which is capable of synthesizing the core 1 O-linked glycan structure Gal β3-GalNAc-Ser/Thr. Previous attempts to measure activity of core 1 β3-galactosyl transferase in vitro and to purify the enzyme have been made. However, previous attempts to sufficiently purify the protein to identify its amino acid sequence or generate antibodies to the enzyme, as well as attempts to identify cDNAs encoding the enzyme, have been unsuccessful. As a result, there has remained a need in the field for complete identification of core 1 β3-galactosyl transferase and of cDNAs encoding core 1 β3-galactosyl transferase.

BRIEF DESCRIPTION OF THE DRAWINGS

FIG. 1 is a table summarizing the purification of core 1 β3-galactosyl transferase from 500 grams of rat liver.

SUMMARY OF THE INVENTION

Figure 2:
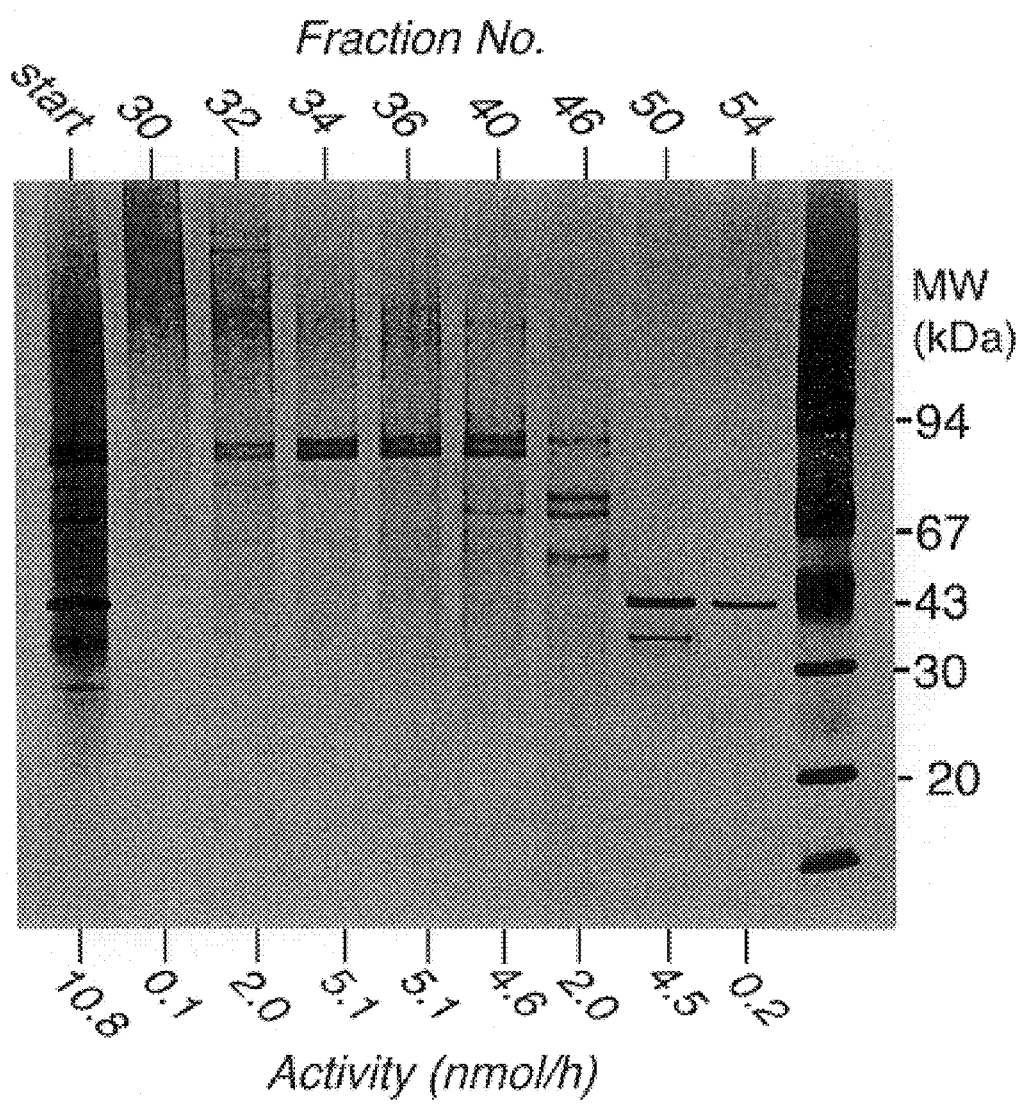
FIG. 2 is a SDS-PAGE gel characterizing the purification of core 1 β3-galactosyl transferase from rat liver.

According to the present invention, core 1 β3-galactosyl transferase and polynucleotides which encode said galactosyl transferase, as well as methods for using same, is provided. Broadly, core 1 β3-galactosyl transferase purified from rat liver is provided, as well as the cloned *Homo sapiens, Rattus norvegicus, Mus musculus, Drosophila melanogaster*, and *Caenorhabditis elegans* cDNAs that encode this enzyme, designated herein as core 1 β3-GalT. The invention further comprises a soluble form of the enzyme.

In one aspect, the invention comprises homologous versions of core 1 β3-GalT proteins encoded by homologous cDNAs, homologous cDNAs, vectors and host cells which express the cDNAs, and methods of using the core 1 β3-GalT proteins and cDNAs.

In further aspects, the present invention contemplates cloning vectors which comprise the nucleic acid of the invention; and prokaryotic or eukaryotic expression vectors which comprise the nucleic acid molecule of the invention operatively associated with an expression control sequence. Accordingly, the invention further relates to a bacterial or eukaryotic cell transfected or transformed with an appropriate expression vector.

An object of the present invention is to provide a nucleic acid, in particular a DNA, that encodes a core 1 β3-galactosyl transferase or a fragment thereof, or homologous derivatives or analogs thereof.

A further object of the present invention, while achieving the before-stated object, is to provide a cloning vector and an expression vector for such a nucleic acid molecule.

Yet another object of the present invention, while achieving the before-stated objects, is to provide a recombinant cell line that contains such an expression vector.

Yet a further object of the present invention, while achieving the before-stated objects, is to produce core 1 β3-galactosyl transferase and fragments thereof.

A still further object of the present invention, while achieving the before-stated objects, is to provide methods for using core 1 β3-galactosyl transferase and fragments thereof.

Other objects, features and advantages of the present invention will become apparent from the following detailed description when read in conjunction with the appended claims.

DETAILED DESCRIPTION OF THE INVENTION

The core 1 O-linked glycan structure, consisting of galactose in β1,3 linkage to N-acetylgalactosamine linked to a threonine or serine on a protein, peptide or polypeptide, is a critical intermediate in the biosynthesis of most extended O-linked glycans. The core 1 structure is found on a number of mucins and adhesion molecules. Core 1 β3-galactosyl transferase, which is capable of synthesizing the core 1 O-linked glycan structure Gal β3-GalNAc-Thr/Ser, has been purified herein from rat liver. N-terminal and internal protein sequence of the purified enzyme was obtained and used to identify human EST clones, and a full length cDNA for the human core 1 β3-galactosyl transferase was isolated using standard molecular biology techniques. The rat core 1 β3-galactosyl transferase cDNA has also been identified. The mouse, *C. elegans*, and two *Drosophila melanogaster* core 1 β3-galactosyl transferase genes are also described herein. An alignment of the human, rat, mouse, *C. elegans*, and two *D. melanogaster* core 1 β3-galactosyl transferases is also provided, demonstrating that these are highly homologous proteins; in particular, the *C. elegans* protein is 41% identical to the human protein, with 7 of 9 cysteines being conserved. Also provided herein is a soluble, epitope-tagged version of the human core 1 β3-galactosyl transferase which has been expressed and recovered from culture media.

The polynucleotides of the present invention may be in the form of RNA or in the form of DNA, wherein the term "DNA" includes cDNA, genomic DNA and synthetic DNA. The DNA may be double-stranded or single-stranded, and if single-stranded, may be the coding strand or non-coding (anti-sense) strand. The coding sequence which encodes the mature polypeptide may be identical to the coding sequence shown herein or may be a different coding sequence which, as a result of the redundancy or degeneracy of the genetic code, encodes the same, mature polypeptide as the DNA coding sequences shown herein.

The polynucleotides which encode the mature polypeptides may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns, or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of the polypeptide having the amino acid sequences of SEQ ID NO:1, SEQ ID NO:3, SEQ ID NO: 5, SEQ ID NO: 7, SEQ ID NO:9 and SEQ ID NO:17. The variants of the polynucleotide may be naturally occurring allelic variants of the polynucleotides or nonnaturally occurring variants of the polynucleotides.

Thus, the present invention includes polynucleotides encoding the same mature polypeptides as shown in SEQ ID NO:1, SEQ ID NO:3, SEQ ID NO: 5, SEQ ID NO: 7, SEQ ID NO:9 and SEQ ID NO:17, as well as variants of such polynucleotides which encode active fragments, derivatives or analogs of said polypeptides. Such nucleotide variants include deletion variants, substitution variants and addition or insertion variants.

As hereinabove indicated, the polynucleotide may have a coding sequence which is a naturally occurring allelic variant of the coding sequences of SEQ ID NO:2, SEQ ID NO:4, SEQ ID NO:6, SEQ ID NO:8, SEQ ID NO:10 and SEQ ID NO:18. The portions of SEQ ID NO:2, SEQ ID NO:4, SEQ ID NO:6, and SEQ ID NO:8 which encode the protein sequences of SEQ ID NO:1, SEQ ID NO:3, SEQ ID NO:5 and SEQ ID NO:7, respectively, are provided as SEQ ID NO:12, SEQ ID NO:13, SEQ ID NO:14, and SEQ ID NO:15, respectively (SEQ ID NO:10 and SEQ ID NO:18 contain only the open reading frames of the core 1 β3-GalT genes and no non-coding sequences). As is known in the art, an allelic variant is an alternate form of a polynucleotide sequence which may have a substitution, deletion or addition of one or more nucleotides which does not substantially adversely alter the function of the encoded polypeptide.

The present invention further relates to a core 1 β3-GalT polypeptide which has the amino acid sequence of SEQ ID NO:1, SEQ ID NO:3, SEQ ID NO: 5, SEQ ID NO: 7, SEQ ID NO:9 and SEQ ID NO:17, as well as fragments, analogs and derivatives of such polypeptide.

The terms "fragment", "derivative" and "analog" when referring to the polypeptide of SEQ ID NO:1, SEQ ID NO:3, SEQ ID NO: 5, SEQ ID NO: 7, SEQ ID NO:9 and SEQ ID NO:17, refer to a β3-GalT which retains essentially the same or increased biological functions or activities as the native core 1 β3-GalT. Thus, an analog includes a proprotein which can be activated by cleavage of a proprotein portion to produce an active mature polypeptide. Fragments of core 1 β3-GalT include soluble, active proteins which have the N-terminal transmembrane region removed.

The polypeptide of the present invention may be a natural polypeptide or a synthetic polypeptide, or preferably a recombinant polypeptide.

The fragment, derivative or analog of the polypeptide of SEQ ID NO:1, SEQ ID NO:3, SEQ ID NO: 5, SEQ ID NO: 7, SEQ ID NO:9 and SEQ ID NO:17 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of one of ordinary skill in the art given the teachings herein.

The polypeptides and polynucleotides of the present invention are preferably provided in an isolated form, and preferably are purified substantially to homogeneity.

The term "isolated" means that the material is removed from its original environment (e.g., the natural environment if it is naturally occurring) in a form sufficient to be useful in performing its inherent enzymatic function. For example, a naturally-occurring polynucleotide or polypeptide present in a living animal is not isolated, but the same polynucleotide or polypeptide separated from some or all of the coexisting materials in the natural system, is isolated. Such polynucleotides could be part of a vector, and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention, and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, or a phage or other vectors known in the art. The engineered host cells can be cultured in conventional nutrient media modified as appropriate for activating promoters, selecting transformants or amplifying the core 1 β3-GalT genes. The culture conditions, such as temperature, pH and the like, are those previously used with the host cell selected for expression, and will be apparent to the ordinary skilled artisan.

The core 1 β3-GalT-encoding polynucleotides of the present invention may be employed for producing Gal β3-GalNAc by recombinant techniques or synthetic in vitro techniques. Thus, for example, the core 1 β3-GalT polynucleotides may be included along with a gene encoding a protein requiring O-linked glycosylation in any one of a variety of expression vectors for expressing the core 1 β3-GalT and the protein requiring O-linked glycosylation. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable in the host. In one embodiment, the protein requiring O-linked glycosylation is P-selectin glycoprotein ligand-1 or a portion thereof or a synthetic peptide which has P-selectin binding activity.

The appropriate DNA sequence (or sequences) may be inserted into the vector by a variety of procedures. For example, the DNA sequence may be inserted into an appropriate restriction endonuclease sites(s) by procedures known in the art. Such procedures and others are deemed to be within the scope of a person of ordinary skill in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells, such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein as described elsewhere herein.

As representative examples of appropriate hosts, there may be mentioned: bacterial cells, such as E. coli, Streptomyces, Salmonella typhimurium; fungal cells, such as yeast; insect cells such as Drosophila and Sf9; animal cells such as CHO, COS, 293T or Bowes melanoma; plant cells, etc. The selection of an appropriate host is deemed to be within the scope of a person of ordinary skill in the art given the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Bacterial: pQE70, pQE60, pQE-9 (Qiagen), pbs, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia). Eukaryotic: PWLNEO, pSV2CAT, pOG44, pXT1, pSG (Stratagene) pSVK3, PBPV, pMSG, pSVL (Pharmacia). However, any other plasmids or vectors may be used as long as they are replicable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cells may be obtained using techniques known in the art. Suitable host cells include prokaryotic or lower or higher eukaryotic organisms or cell lines, for example bacterial, mammalian, yeast, or other fungi, viral, plant or insect cells. Methods for transforming or transfecting cells to express foreign DNA are well known in the art (See for example, Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,766,075; and Sambrook et al., Molecular Cloning: A Laboratory Manual 2nd Ed., Cold Spring Harbor Laboratory Press, 1989), all of which are incorporated herein by reference.

Introduction of the construct into the host cell can be effected by methods well known in the art such as by calcium phosphate transfection, DEAE-Dextran mediated transfection, or electroporation (Davis, L., Dibner, M. Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated herein by reference.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples include the SV40 enhancer, a cytomegalovirus early promoter enhancer, the polyoma enhancer, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracelluar medium. Optionally, the heterologous sequence can encode a fusion protein including an N-terminal or C-terminal identification peptide imparting desired characteristics, e.g., stabilization or simplified purification of expressed recombinant product.

Useful expression vectors for bacterial use are constructed by inserting one or more structural DNA sequences encoding one or more desired proteins together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322, (ATCC 37017). These pBR322 "backbone" sections are combined with an appropriate promoter and the structural sequence to be expressed.

Following transformation of a suitable host strain and growth of the host strain to an appropriate cell density, the selected promoter is induced by appropriate methods (e.g., temperature shift or chemical induction) and cells are cultured for an additional period.

Cells are typically harvested by centrifugation, disrupted by physical or chemical methods, and the resulting crude extract retained for further purification. Microbial cells employed in expression of proteins can be disrupted by any convenient method, including freeze-thaw cycling, sonication, mechanical disruption, or use of cell lysing agents. Such methods are well known to a person of ordinary skill in the art.

Various mammalian cell culture systems can also be employed to express recombinant protein. Examples of mammalian expression systems include the COS-7 lines of monkey kidney fibroblasts, described by Gluzman (Cell, 23:175 (1981)), and other cell lines capable of transcribing compatible vectors, for example, the C127, 293T, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

The core 1 $\beta$3-GalT polypeptides or portions thereof can be recovered and purified from recombinant cell cultures by methods including but not limited to ammonium sulfate or ethanol precipitation, acid extraction, anion or cation exchange chromatography, phosphocellulose chromatography, hydrophobic interaction chromatography, affinity chromatography, hydroxyl apatite chromatography, and lectin chromatography, alone or in combination. Protein refolding steps can be used as necessary in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

A recombinant core 1 $\beta$3-GalT of the invention, or functional fragment, derivative or analog thereof, may be expressed chromosomally, after integration of the core 1 $\beta$3-GalT coding sequence by recombination. In this regard any of a number of amplification systems may be used to achieve high levels of stable gene expression (See Sambrook et al., 1989, supra).

The cell into which the recombinant vector comprising the nucleic acid encoding the core 1 $\beta$3-GalT is cultured in an appropriate cell culture medium under conditions that provide for expression of the core 1 $\beta$3-GalT by the cell. If full length core 1 $\beta$3-GalT is expressed, the expressed protein will comprise an integral transmembrane portion. If a core 1 $\beta$3-GalT lacking a transmembrane domain is expressed, the expressed soluble core 1 $\beta$3-GalT can then be recovered from the culture according to methods well known to persons of ordinary skill in the art. Such methods are described in detail, infra.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab (F(ab')2 fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by other appropriate forms of administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The polyclonal or monoclonal antibodies may be labeled with a detectable marker including various enzymes, fluorescent materials, luminescent materials and radioactive materials. Examples of suitable enzymes include horseradish peroxidase, alkaline phosphatase, $\beta$-galactosidase, or acetylcholinesterase; examples of suitable fluorescent materials include umbeliferone, fluorescein, fluorescein isothiocyanate, rhodamine, dichlorotriazinylamine fluorescein, dansyl chloride or phycoerythrin; examples of luminescent materials include luminol and aequorin; and examples of suitable radioactive material include $S^{35}$, $Cu^{64}$, $Ga^{67}$, $Zr^{89}$, $Ru^{97}$, $Tc^{99m}$, $Rh^{105}$, $Pd^{109}$, $In^{111}$, $I^{123}$, $I^{125}$, $I^{131}$, $Re^{186}$, $Au^{198}$, $Au^{199}$, $Pb^{203}$, $At^{211}$, $Pb^{212}$ and $Bi^{212}$. The antibodies may also be labeled or conjugated to one partner of a ligand binding pair. Representative examples include avidin-biotin and riboflavin-riboflavin binding protein.

Methods for conjugating or labeling the antibodies discussed above with the representative labels set forth above may be readily accomplished using conventional techniques such as described in U.S. Pat. No. 4,744,981 (Trichothecene Antibody); U.S. Pat. No. 5,106,951 (Antibody Conjugate); U.S. Pat. No. 4,018,884 (Fluorengenic Materials and Labeling Techniques); U.S. Pat. No. 4,897,255 (Metal Radionucleotide Labeled Proteins for Diagnosis and Therapy); U.S. Pat. No. 4,988,496 (Metal Radionuclide Chelating Compounds for Improved Chelation Kinetics); Inman, Methods in Enzymology, Vol. 34, Affinity Techniques, Enzyme Purification; Part B, Jacoby and Wichek (eds) Academic Press, New York, P. 30, 1974; and Wilcheck and Bayer, The Avidin-Biotin Complex in Bioanalytical Applications Anal. Biochem. 171:1–32, 1988.

Due to the degeneracy of nucleotide coding sequences, other DNA sequences which encode substantially the same amino acid sequence as a core 1 β3-GalT gene described herein may be used in the practice of the present invention. These include but are not limited to nucleotide sequences comprising all or portions of core 1 β3-GalT genes which are altered by the substitution of different codons that encode the same amino acid residue within the sequence, thus producing a silent change. Likewise, the core 1 β3-GalT derivatives of the invention include, but are not limited to those containing, as a primary amino acid sequence, all or part of the amino acid sequence of the core 1 β3-GalT protein including altered sequences in which functionally equivalent amino acid residues are substituted for residues within the sequence, resulting in a conservative amino acid substitution. For example, one or more amino acid residues within the sequence can be substituted for another amino acid of a similar polarity, which acts as a functional equivalent. Substitutions for an amino acid within the sequence may be selected from, but are not limited to, other members of the class to which the amino acid belongs. For example, the nonpolar (hydrophobic) amino acids include alanine, leucine, isoleucine, valine, proline, phenylalanine, tryptophan and methionine. The polar (neutral) amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding core 1 β3-GalT derivatives and analogs of the invention can be produced by various methods known in the art. The manipulations which result in their production can occur at the gene or protein level. For example, the cloned core 1 β3-GalT gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of core 1 β3-GalT, care should be taken to ensure that the modified gene remains within the same translational reading frame as the core 1 β3-GalT coding sequence, uninterrupted by translation stop signals, in the gene region where the desired activity is encoded.

Within the context of the present invention, core 1 β3-GalT may include various structural forms of the primary protein which retain biological activity. For example, core 1 β3-GalT polypeptide may be in the form of acidic or basic salts or in neutral form. In addition, individual amino acid residues may be modified by oxidation or reduction. Furthermore, various substitutions, deletions or additions may be made to the amino acid or nucleic acid sequences, the net effect being that biological activity of core 1 β3-GalT is retained. Due to code degeneracy, for example, there may be considerable variation in nucleotide sequences encoding the same amino acid.

Mutations in nucleotide sequences constructed for expression of derivatives of core 1 β3-GalT polypeptide must preserve the reading frame phase of the coding sequences. Furthermore, the mutations will preferably not create complementary regions that could hybridize to produce secondary mRNA structures, such as loops or hairpins which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site specific mutagenesis procedures may be employed to provide an altered gene having particular codons altered according to the substitution, deletion, or insertion required. Deletions or truncations of core 1 β3-GalTs may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al., (Molecular Cloning: A Laboratory Manual, 2nd Ed., Cold Spring Harbor Laboratory Press, 1989).

As noted above, a nucleic acid sequence encoding a core 1 β3-GalT can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated core 1 β3-GalT gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR Technology: Principles and Applications for DNA amplification, H. Erlich, ed., Stockton Press, Chapter 6, pp. 61–70).

It is well known in the art that some DNA sequences within a larger stretch of sequence are more important than others in determining functionality. A skilled artisan can test allowable variations in sequence, without expense of undue experimentation, by well-known mutagenic techniques which include, but are not limited to, those discussed by D. Shortle et al. (1981) Ann. Rev. Genet. 15:265; M. Smith (1985) ibid. 19:423; D. Botstein and D. Shortle (1985) Science 229:1193; by linker scanning mutagenesis (S. McKnight and R. Kingsbury (1982) Science 217:316), or by saturation mutagenesis (R. Myers et al. (1986) Science 232:613). These variations may be determined by standard techniques in combination with assay methods described herein to enable those in the art to manipulate and bring into utility the functional units of upstream transcription activating sequence, promoter elements, structural genes, and polyadenylation signals. Using the methods described herein the skilled artisan can without application of undue experimentation test altered sequences within the upstream activator for retention of function. All such shortened or altered functional sequences of the activating element sequences described herein are within the scope of this invention.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other species which possess core 1 β3-GalT activity. The PCR amplified sequences can be examined to determine the relationship between the various core 1 β3-GalT genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides of the nucleic acid molecule of the invention which occur naturally, as in purified products of restriction endonuclease digest, or are produced synthetically using techniques known in the art, such as phosphotriester and phosphodiesters methods (See Good et al., Nucl. Acid Res 4:2157, 1977) or automated techniques (See for example, Conolly, B. A. Nucleic Acids Res. 15:15(8\7): 3131, 1987). The primers are capable of acting as a point of initiation of synthesis when placed under conditions which permit the synthesis of a primer extension product which is complementary to the DNA sequence of the invention i.e., in the presence of nucleotide substrates, an agent for polymerization, such as DNA polymerase, and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using to prepare amplification products. The primer preferably contains between about 7 and 50 nucleotides.

The primers may be labeled with detectable markers which allow for detection of the amplified products. Suitable detectable markers are radioactive markers such as $P^{32}$, $S^{35}$, $I^{125}$, and $H^3$, luminescent markers such as chemiluminescent markers, preferably luminol, and fluorescent markers, preferably dansyl chloride, fluorocein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide sequence thereof which is to be amplified. Restriction site linkers may also be incorporated into the primers, allowing for digestion of the amplified products with the appropriate restriction enzymes facilitating cloning and sequencing of the amplified product.

In an embodiment of the invention a method of determining the presence of a nucleic acid molecule having a sequence encoding a core 1 β3-GalT, or a predetermined oligonucleotide fragment thereof in a sample, is provided comprising treating the sample with primers which are capable of amplifying the nucleic acid molecule or the predetermined oligonucleotide fragment thereof in a polymerase chain reaction to form amplified sequences, under conditions which permit the formation of amplified sequences, and assaying for amplified sequences.

The polymerase chain reaction refers to a process for amplifying a target nucleic acid sequence as generally described in Innis et al., Academic Pres, 1990; in Mullis et. al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications, M. A. Innis, D. H. Gelfand, J. J. Shinsky and T. J. White eds, pp 3–12, Academic Press 1989, which is also incorporated herein by reference.

It will be appreciated that other techniques such as the Ligase Chain Reaction (LCR) and NASBA may be used to amplify a nucleic acid molecule of the invention. In LCR, two primers which hybridize adjacent to each other on the target strand are ligated in the presence of the target strand to produce a complementary strand (Barney in "PCR Methods and Applications", August 1991, Vol 1(1), page 4, and European Published Application No. 0320308, published Jun. 14, 1989. NASBA is a continuous amplification method using two primers, one incorporating a promoter sequence recognized by an RNA polymerase and the second derived from the complementary sequence of the target sequence to the first primer (U.S. Pat. No. 5,130,238 to Malek).

The present invention also provides novel fusion proteins in which any of the enzymes of the present invention are fused to a polypeptide such as protein A, streptavidin, fragments of c-myc, maltose binding protein, IgG, IgM, amino acid tag, etc. In addition, it is preferred that the polypeptide fused to the enzyme of the present invention is chosen to facilitate the release of the fusion protein from a prokaryotic cell or a eukaryotic cell, into the culture medium, and to enable its (affinity) purification and possibly immobilization on a solid phase matrix.

In another embodiment, the present invention provides novel DNA sequences which encode a fusion protein according to the present invention.

The present invention also provides novel immunoassays for the detection and/or quantitation of the present enzymes in a sample. The present immunoassays utilize one or more of the present monoclonal or polyclonal antibodies which specifically bind to the present enzymes. Preferably the present immunoassays utilize a monoclonal antibody. The present immunoassay may be a competitive assay, a sandwich assay, or a displacement assay, such as those described in Harlow, E. et al., *Antibodies. A Laboratory Manual*, Cold Spring Harbor Laboratory Press, Cold Spring Harbor, N.Y. (1988) and may rely on the signal generated by a radiolabel, a chromophore, or an enzyme, such as horseradish peroxidase.

Alterations in core 1 β3-galactosyl transferase activity have been described in Tn-syndrome (Vainchenker et al. (1985) J. Clin. Invest. 75:541), an exceedingly rare hematologic disorder, which has been described in probably less than 50 patients. In addition, a role for an alteration in the synthesis of the core 1 structure has been proposed as a possible etiology for IgA nephropathy syndrome, although this remains to be proven (Kokubo et al. (1997) J. Am. Soc. Nephrol. 8:915). Core 1 β3-galactosyl transferase has also been demonstrated to be useful in the synthesis of glycosulfopeptides which can function as inhibitors of P-selectin:PSGL-1 interactions.

Therefore, the core 1 β3-galactosyl transferase enzymes of the present invention can be used for in vitro synthesis of glycosulfopeptides to block selectin:ligand interactions. Other potential uses for the core 1 3-galactosyl transferase enzymes of the present invention which can be envisioned include diagnostic tests for the rare Tn-syndrome or IgA nepropathy, as well as for therapy of these disorders.

The invention will be more fully understood by reference to the following examples. However, the examples are merely intended to illustrate embodiments of the invention and are not to be construed to limit the scope of the invention.

EXAMPLES

Assay of Core 1 133-Galactosyl Transferase Activity. Core 1 β3-galactosyl transferase activity was assayed as previously described (Brockhausen, I. (1992) Biochem and Cell Biol 70:99) with the following modifications. The assay contained the following: 100 mM MES pH 6.8, 0.2% Triton X-100, 20 mM $MnCl_2$, 1 mM phenyl-α-GalNAc, 4 mM [$^3$H]-UDP-Gal (100,000–150,000 dpm/nmol), 2 mM ATP and 5–25 µl sample containing core 1 β3-GalT in a total volume of 50 µl. Mixtures were incubated at 37° C. for 30–60 minutes and stopped by adding 950 µl cold $H_2O$. The mixtures were loaded onto 500 mg Sep-Pak® C18 cartridges previously activated with 2 ml ethanol and equilibrated with 10 ml water. Following application of the diluted reaction mixture, the columns were washed with 10 ml water, eluted with 1 ml n-butanol, and radioactivity determined by liquid scintillation counting in 10 ml Scintiverse-BD.

Purification of Core 1 β33-Galactosyl Transferase. The enzyme has been purified from rat liver using an affinity chromatographic step consisting of immobilized bovine submaxillary mucin that has been neuraminidase treated and coupled to UltraLink™. The enzyme binds tightly to this support and is eluted with high salt. Due to the tight binding, core 1 β3-GalT elutes late in the elution pattern after most nonspecific binding proteins have already eluted. Final purification was achieved by gel filtration chromatography on Superose 12. Overall, the enzyme was purified 71,000-fold in 8% yield, as shown in FIGS. 1 and 2.

Step 1: Homogenization, Subcellular Fractionation, Isolation of Membranes and Solubilization. 500 grams fresh rat liver was washed with cold 150 mM NaCl in 25 mM Tris-HCl pH 7.4 and homogenized with 2,000 ml of buffer containing 25 mM Tris-HCl pH 7.5, 0.25 M Sucrose, 1 mM PMSF, 2 µg/ml Leupeptin, 1 mM Benzamidine, and 0.7 µg/ml Pepstatin A in a Waring commercial blender. The homogenate was centrifuged at 20,000×g for 20 minutes, and the supernatant was then decanted and centrifuged at 100,000×g for 60 minutes. The pellets were suspended in 5 volumes of buffer containing 50 mM Tris-HCl pH 9.0, 0.25 M Sucrose, 1 mM PMSF, 1 mM Benzamidine, 0.7 µg/ml Pepstatin A, and 2 µg/ml Leupeptin. The suspension was sonicated four times for 10 seconds each in an ice-bath, extracted in ice for 1 hour, and then centrifuged at 100,000×g for 60 minutes. The supernatant was collected and the pH adjusted using 1 mM MES. The approximate volume of the supernatant containing solubilized membrane proteins was 1,000 ml.

Step 2: SP-Sepharose FF Chromatography. The solubilized membrane proteins were applied onto a 6×20 cm SP-Sepharose FF column (Pharmacia BioTech) which was equilibrated with equilibration buffer, which contains 25 mM MES pH 6.5, 0.1% Triton X-100, 5 mM $MnCl_2$, 1 mM PMSF, 1 mM Benzamidine, 0.7 µg/ml Pepstatin A, and 2 µg/ml Leupeptin. The column was washed with the same buffer, and then the core 1 β3-GalT was step-eluted using 1 M NaCl in equilibration buffer.

Step 3: Asialo-BSM UltraLink™ Chromatography. The SP-Sepharose elute was dialyzed and concentrated into equilibration buffer in an Amicon concentrator using a YM30 membrane. The sample was loaded onto a 1×5 cm Asialo-BSM Ultralink™ column equilibrated with a second equilibration buffer, which contains 25 mM MES pH 6.8, 0.01% Triton X-100, 10 mM $MnCl_2$, 150 mM NaCl, 1 mM PMSF, 1 mM Benzaminidine, 2 µg/ml Leupeptin, and 0.7 µg/ml Pepstatin A. After washing with the same buffer, core 1 β3-GalT was eluted with 1 M NaCl in the second equilibration buffer without $MnCl_2$. Fractions were collected, and activity of core 1 β3-GalT was assayed as described above. The fractions which contained core 1 β3-GalT were then pooled.

Step 4: Superose 12 Chromatography. The pooled samples containing core 1 β3-GalT from Asialo-BSM UltraLink™ chromatography were concentrated to a final volume of 200 µl using Centriprep 30 and Centricon 30 concentrators, loaded on a 1.5×35 cm Superose 12 column (Pharmacia BioTech) equilibrated with a third equilibration buffer, which contains 25 mM Tris-HCl pH 7.2, 0.005% Triton X-100, and 150 mM NaCl. Core 1 β3-GalT was eluted with the same buffer, and fractions were pooled and assayed as described above.

Using the purified enzyme, amino-terminal and internal protein sequence was obtained by standard molecular biology techniques. BlastP searching of the NCBI EST database using the rat core 1 β3-GalT N-terminal peptide sequence identified a rat EST, AI059600.

Identification of Human Core 1 β3-GalT and Expression of Recombinant Core 1 β3-GalT in Mammalian Cells. BlastN searching with the rat EST sequence (AI059600) identified a human EST (T10488). The human EST was sequenced and found to contain a 1.6 kb insert incomplete at the 5' end. The human core 1 β3-GalT cDNA was complete by 5'-RACE using primers AP1 and 5'CTTTATGTTGGCTAGAATCTGC-3' (SEQ ID NO:23) with human placental marathon-ready cDNA as template. Amplification was carried out at 94° C. for 1 minute followed by 35 cycles of 94° C. for 30 seconds and 68° C. for 2 minutes, then the reaction was held at 68° C. for 10 minutes. The 450 bp product was purified using a QIA-quick column, ligated into PCR2.1, and sequenced.

Figure 3:
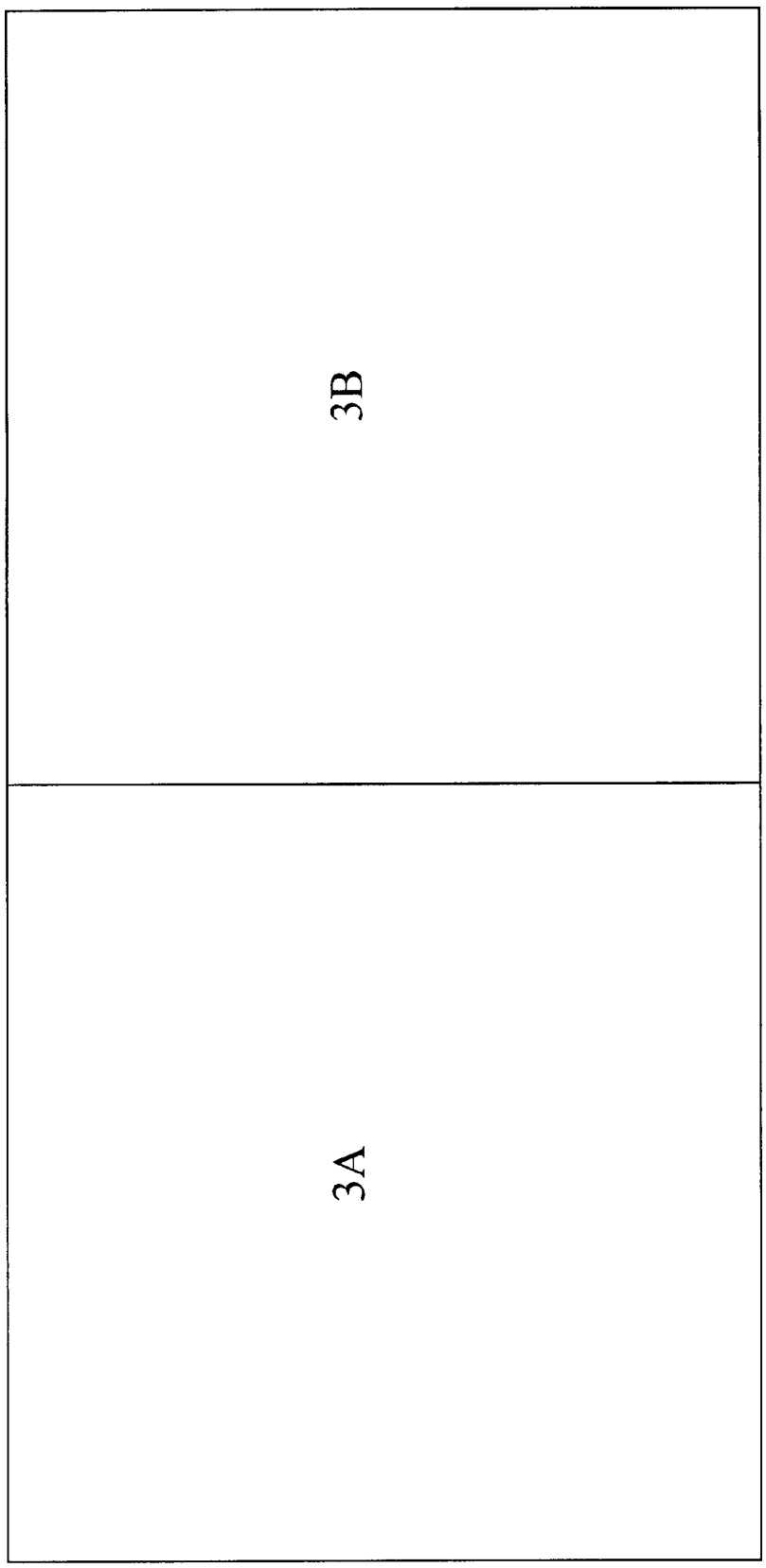
FIG. 3 shows the cDNA (SEQ ID NO:2) and protein sequence (SEQ ID NO:1) of human core 1 β3-galactosyl transferase.

The 1794 bp cDNA encoding human core 1 β3-GalT is shown in SEQ ID NO:2. The cDNA (SEQ ID NO:2) and protein sequence (SEQ ID NO:1) of human core 1 β3-GalT is shown in FIG. 3. An open reading frame (SEQ ID NO:12) of SEQ ID NO:2 encodes a 363 amino acid type 2 transmembrane protein. The predicted 28 amino acid transmembrane domain (SEQ ID NO:16) is underlined in FIG. 3.

An expression vector encoding the wild-type human core 1 β3-Gal-T was constructed by ligating a 1.5 kb XbaI/XhoI fragment of EST T10488 with a BamHI/XhoI digested pcDNA3.1(+) vector (Invitrogen), a 155 bp ApoI/XbaI fragment from the cloned 5'-RACE product, and annealed oligonucleotides 5'-GATCCACCATGGCCTCTAAATCCTGGCTG-3' (SEQ ID NO: 19) and 5'-AATTCAGCCAGGATTTAGAGGCCATGGTG-3' (SEQ ID NO:20).

Human embryonic kidney 293-T cells in 100 mm dishes were transiently transfected with wild-type expression vector using FuGENE™6 according to the manufacturer's protocol and cultured in low-glucose Dulbecco's modified Eagle's media containing 10% Fetal Calf Serum. Cells were harvested at 24, 48 and 72 h, washed twice with cold TBS (25 mM Tris-HCl pH 7.4, 150 mM NaCl) and sonicated on ice (10 seconds, 3 times, Branson Cell Disruptor model 185, setting 5) in 300–500 μl of TBS containing 1 mM PMSF, 1 mM benzaminidine-HCl, 2 μg/ml leupeptin. Membrane fragments were collected by centrifugation (14,000 rpm for 10 minutes), solubilized in 0.5% Triton X-100, and assayed for core 1 β3-GalT as described hereinbefore.

Expression of Recombinant Soluble, Epitope-Tagged Core 1 β3-GalT in Mammalian Cells. An expression vector encoding soluble epitope-tagged core 1 β3-GalT was constructed by ligating a 1584 bp BsmI/XhoI fragment from EST T10488 with BamHI/XhoI digested pcDNA3.1(+)-TH (a modified form of the pcDNA3.1(+) vector constructed for expression of fusion proteins containing an $NH_2$-terminal epitope for HPC4, a $Ca^{2+}$-dependent monoclonal antibody to Protein C (Rezaie et al. (1992) J. Biol. Chem. 267:26104)), and annealed oligonucleotides 5'-GATCCTCATGCAAGG-3' (SEQ ID NO:21) and 5'-TTGCATGAG-3' (SEQ ID NO:22). Expression of this plasmid in eucaryotic cells results in the synthesis of core 1 β3-GalT with 31 additional amino acids fused to Asp45 of the human core 1 β3-GalT sequence (SEQ ID NO:11). The first 19 additional amino acids (SEQ ID NO:24) correspond to the human transferrin signal peptide, which is recognized during the sorting process and directs the transport of the protein to the cell surface for secretion from the cell. Additional amino acids 20–31 (SEQ ID NO:25) correspond to the HPC4 epitope tag. The soluble form of core 1 β3-GalT which is secreted from the cell will have the signal peptide sequence removed but will still contain the HPC4 epitope tag.

Capture Assay for Soluble Form of Core 1 β3-GalT. Human 293T cells were transfected with the soluble form of core 1 β3-GalT and cultured and harvested as described hereinbefore for expression for wild type core 1 β3-GalT. Following harvesting at 24, 48 and 72 h, the cells were directly assayed as described herein below.

HPC4-Affi-Gel 10 (15 μl) equilibrated with equilibration buffer (50 mM Tris-HCl pH 7.2, 100 mM NaCl and 1 mM $CaCl_2$) was incubated with 500 μl media at 4° C. on a rotator for 2 h, spun for 5 minutes in a microcentrifuge at 14,000×g, and both beads and supernatant were collected and saved. The beads were washed three times with 500 μl of 50 mM Tris-HCl pH 7.4, 1 mM NaCl, 1 mM $CaCl_2$ and once with equilibration buffer. The beads, media and supernatant were then assayed in the absence of Triton X-100 for core 1 β3-GalT activity as described herein before.

Identification of Core 1 β3-Galactosyl Transferase Gene and Protein Sequences in Other Species and Homology to Human Core 1 β3-GalT. M. musculus, C. elegans and D. melanogaster genes are described herein which encode core 1 β3-galactosyl transferases. The 1469 bp M. musculus cDNA is shown in SEQ ID NO:6, and an open reading frame corresponding to bases 180–1271 of SEQ ID NO:6, shown in SEQ ID NO:14, encodes the protein sequence of M. musculus core 1 β3-GalT (SEQ ID NO:5). The M. musculus core 1 β3-GalT has 89% identity and 94% similarity to the human enzyme (SEQ ID NO:1). The 1172 bp C. elegans core 1 β3-GalT gene is shown in SEQ ID NO:8, and an open reading frame corresponding to bases 1–1170 of SEQ ID NO:8, shown in SEQ ID NO:15, encodes the protein sequence of C. elegans core 1 β3-GalT (SEQ ID NO:7). The C. elegans core 1 β3-GalT has 41% identity and 58% similarity to the human enzyme (SEQ ID NO:1). Two highly homologous sequences derived from D. melanogaster have been identified and are designated as D. melanogaster core 1 β3-GalT #1 and #2, respectively. The 1167 bp open reading frame of the D. melanogaster core 1 β3-GalT #1 gene is shown in SEQ ID NO: 18, and encodes the protein sequence of D. melanogaster core 1 β3-GalT #1 (SEQ ID NO:17). The 1104 bp open reading frame of the D. melanogaster β3-GalT #2 gene is shown in SEQ ID NO:10, and encodes the protein sequence of D. melanogaster core 1 β3-GalT #2 (SEQ ID NO:9). The D. melanogaster core 1 β3-GalT #2 has 41% identity and 55% similarity to the human enzyme (SEQ ID NO:1).

In addition, a cDNA for the rat (R. norvegicus) core 1 β3-GalT has also been identified herein and is shown in SEQ ID NO:4. Bases 154–1245 of SEQ ID NO:4 correspond to the open reading frame, shown in SEQ ID NO: 13, which encodes the protein sequence of R. norvegicus core 1 β3-GalT, which is shown in SEQ ID NO:3. The rat core 1 β3-GalT has 89% identity and 93% similarity to the human enzyme (SEQ ID NO:1).

It will be appreciated that the invention includes nucleotide or amino acid sequences which have substantial sequence homology (identity) with the nucleotide and amino acid sequences shown in the Sequence Listings. The term "sequences having substantial sequence homology" includes those nucleotide and amino acid sequences which have slight or inconsequential sequence variations from the sequences disclosed in the Sequence Listings, i.e. the homologous sequences function in substantially the same manner to produce substantially the same polypeptides as the actual sequences. The variations may be attributable to local mutations or structural modifications.

Substantially homologous (identical) sequences further include sequences having at least 41% sequence homology (identity) with the β3-GalT polynucleotide or polypeptide sequences shown herein or other percentages as defined elsewhere herein.

As noted elsewhere herein, the present invention includes polynucleotides represented by SEQ ID NO:2, SEQ ID NO:4, SEQ ID NO:6, SEQ ID NO:8, SEQ ID NO:10 and SEQ ID NO:18, and coding sequences thereof (SEQ ID NO:12, SEQ ID NO:13, SEQ ID NO:14, SEQ ID NO:15, SEQ ID NO:10 and SEQ ID NO:18, respectively), which encode the proteins of SEQ ID NO:1, SEQ ID NO:3, SEQ ID NO:5, SEQ ID NO:7, SEQ ID NO:9 and SEQ ID NO:17, respectively.

Each polynucleotide comprises untranslated regions upstream and/or downstream of the coding sequence and a coding sequence (which by convention includes the stop codon). The coding sequences in SEQ ID NO:12, SEQ ID NO:13, SEQ ID NO:14, SEQ ID NO:15, SEQ ID NO:10 and SEQ ID NO:18 of each polynucleotide SEQ ID NO:2, SEQ ID NO:4, SEQ ID NO:6, SEQ ID NO:8, SEQ ID NO: 10 and SEQ ID NO: 18, respectively, encodes polypeptides of 363, 363, 363, 389, 367 and 388 amino acids, respectively (SEQ ID NO:1, SEQ ID NO:3, SEQ ID NO:5, SEQ ID NO:7, SEQ ID NO:9, and SEQ ID NO:17).

A comparison of the core 1 β3-GalTs identified herein revealed considerable homology in specific portions of the amino acid sequences. Each core 1 β3-GalT of SEQ ID NO:3, SEQ ID NO:5, SEQ ID NO:7, SEQ ID NO:9 and SEQ ID NO:17 had homologous loci which had 100% identity with amino acid residues 120–123, 167–173, 208–213, 254–259, 271–275, and 307–311 of SEQ ID NO:1 (h-β3-GalT). The core 1 β3-GalTs further had homologous loci having at least 60%, 67% and 63% identity with hβ3-GalT amino acid residues 97–126, 143–224, and 239–330, respectively.

Figure 4:
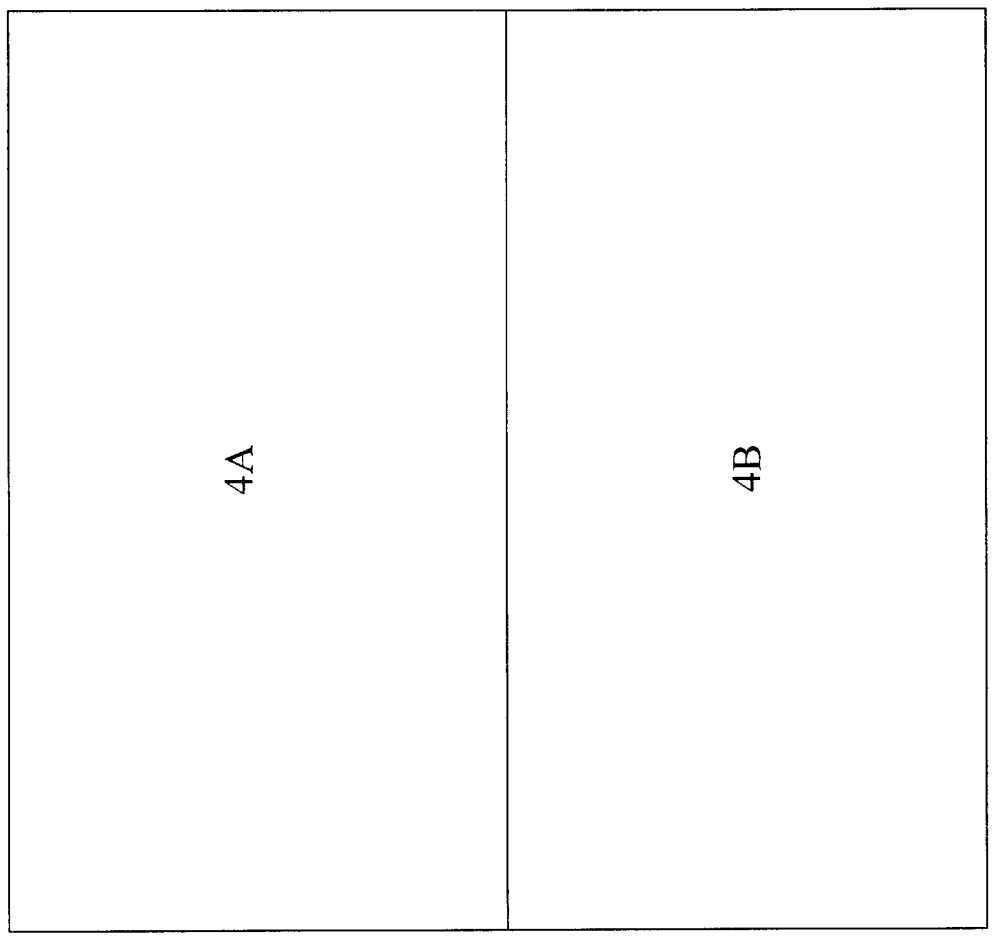
FIG. 4 is an alignment comparison of human (SEQ ID NO:1), rat (SEQ ID NO:3), mouse (SEQ ID NO:5), two *D. melanogaster* (SEQ ID NO:9 and SEQ ID NO:17) and *C. elegans* (SEQ ID NO:7) core 1 β3-galactosyl transferase protein sequences.
Figure 4B:
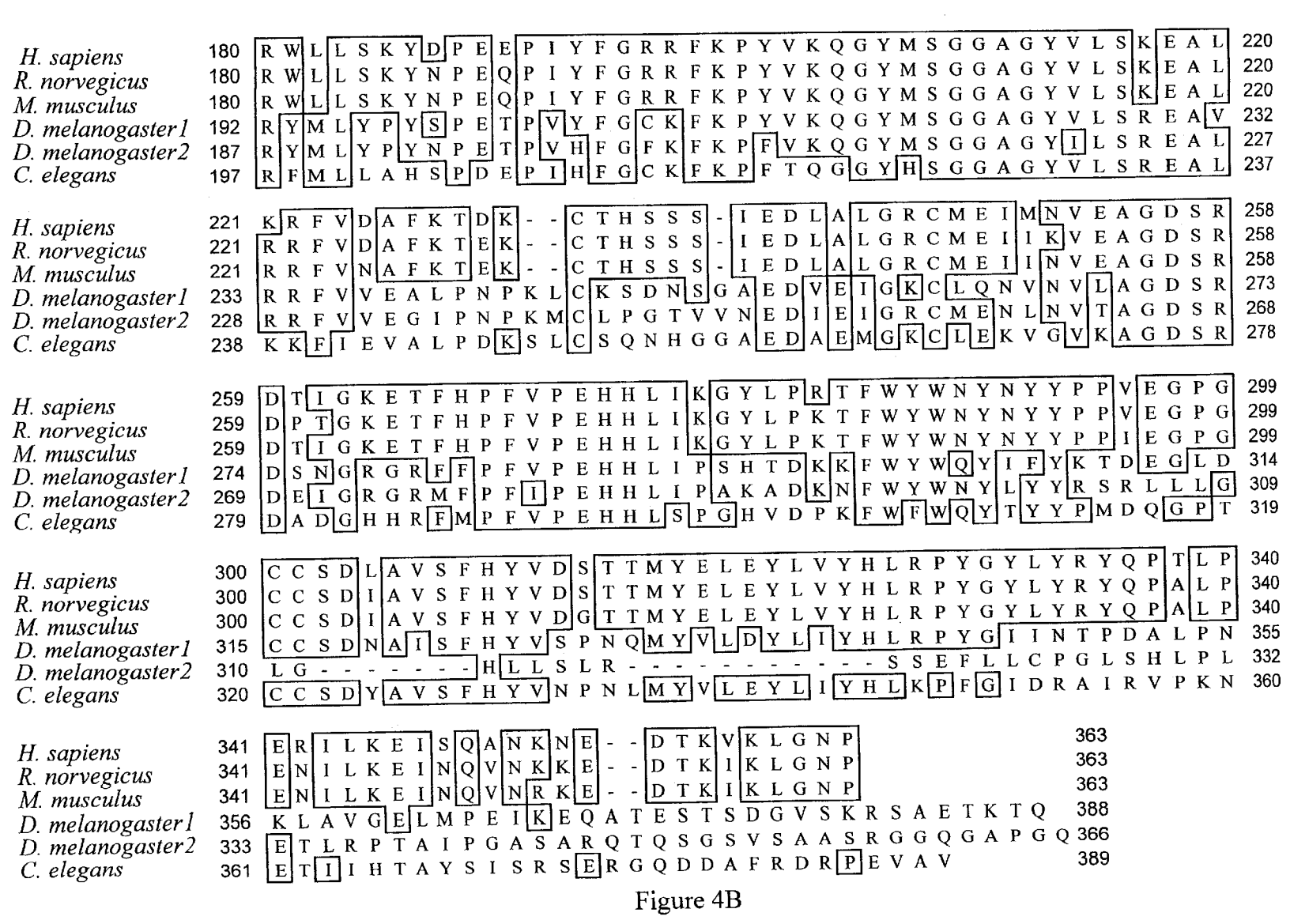

A comparison of the overall homology of the core 1 β3-GalTs identified herein further reveals a considerable range in homology as indicated in the alignment in FIG. 4.

Homologies provided herein were calculated by ClustalW, a program component of MacVector Version 6.5 by the Genetics Computer Group at University Research Park, 575 Science Dr., Madison, Wis. 53711.

The term "identity" or "homology" used herein is defined by the output called "Percent Identity" of a computer alignment program called ClustalW. "Similarity" values provided herein are also provided as an output of the ClustalW program using the alignment values provided below. As noted, this program is a component of widely used package of sequence alignment and analysis programs called MacVector Version 6.5, Genetics Computer Group (GCG), Madison, Wis. The ClustalW program has two alignment variables, the gap creation penalty and the gap extension penalty, which can be modified to alter the stringency of a nucleotide and/or amino acid alignment produced by the program. The settings for open gap penalty and extend gap penalty used herein to define identity for amino acid alignments were as follows:

Open Gap penalty=10.0

Extend Gap penalty=0.05

Delay Divergent=40%

The program used the BLOSUM series scoring matrix. Other parameter values used in the percent identity determination were default values previously established for the 6.5 version of the ClustalW program. (see Thompson, J. D. et al (1994) Nucleic Acids Res 22:4673).

In general, polynucleotides which encode core 1 β3-galactosyl transferases are contemplated by the present invention. In particular, the present invention contemplates DNA sequences having SEQ ID NO: 2, SEQ ID NO:4, SEQ ID NO:6, SEQ ID NO:8, SEQ ID NO:10 and SEQ ID NO:18, and DNA sequences comprising bases 63–1154 of SEQ ID NO:2 (SEQ ID NO:12), bases 154–1245 of SEQ ID NO:4 (SEQ ID NO:13), bases 180–1271 of SEQ ID NO:6 (SEQ ID NO:14), and bases 1–1170 of SEQ ID NO:8 (SEQ ID NO:15). The invention further comprises portions of said sequences which encode soluble forms of core 1 β3-GalTs.

The invention further contemplates DNA sequences which comprise portions of polynucleotides of SEQ ID NO:12, SEQ ID NO:13, SEQ ID NO:14, SEQ ID NO: 15, SEQ ID NO: 10 and SEQ ID NO: 18 which encode soluble proteins having core 1 β3-galactosyl transferase activity. That is, portions of the above polynucleotides which encode the N-terminal transmembrane region have been removed, and the remaining portions encode soluble proteins having core 1 β3-galactosyl transferase activity.

The invention further contemplates polynucleotides which are at least about 50% homologous, 60% homologous, 70% homologous, 80% homologous or 90% homologous to the coding sequence SEQ ID NO:12, where homology is defined as strict base identity, wherein said polynucleotides encode proteins having core 1 β3-galactosyl transferase activity.

The present invention further contemplates nucleic acid sequences which differ in the codon sequence from the nucleic acids defined herein due to the degeneracy of the genetic code, which allows different nucleic acid sequences to code for the same protein as is further explained herein above and as is well known in the art. The polynucleotides contemplated herein may be DNA or RNA. The invention further comprises DNA or RNA nucleic acid sequences which are complementary to the sequences described above.

The present invention further comprises polypeptides which are encoded by the polynucleotide sequences described above. In particular, the present invention contemplates polypeptides having core 1 β3-galactosyl transferase activity including SEQ ID NO: 1, SEQ ID NO:3, SEQ ID NO:5, SEQ ID NO:7, SEQ ID NO:9 and SEQ ID NO:17 and versions thereof which lack the transmembrane domain and which are therefore soluble. The invention further contemplates polypeptides which are at least 41% homologous, 50% homologous, 60% homologous, 70% homologous, 80% homologous, or 90% homologous to the polypeptides represented herein by SEQ ID NO:1 or SEQ ID NO:3, wherein homology is defined as strict identity. The present invention further contemplates polypeptides having loci in substantially homologous positions which have at least 60% or greater identity with residues 97–126, 67% or greater identity with residues 143–224, and 63% or greater identity with residues 239–330 of SEQ ID NO:1, and which have core 1 β3-galactosyl transferase activity. The present invention further contemplates polypeptides which differ in amino acid sequence from the polypeptides defined herein by substitution with functionally equivalent amino acids, resulting in what are known in the art as conservative substitutions, as discussed above herein.

Also included in the invention are isolated DNA sequences which hybridize to the DNAs set forth in SEQ ID NO:2, SEQ ID NO:4, SEQ ID NO:6, SEQ ID NO:8, SEQ ID NO: 10 or SEQ ID NO: 18 under stringent or relaxed conditions (as well known to persons of ordinary skill in the art), and which have core 1 β3-galactosyl transferase activity.

In summary, as shown herein, at least three mammalian core 1 β3-galactosyl transferases, a *C. elegans* core 1 β3-galactosyl transferase and two *D. melanogaster* core 1 β3-galactosyl transferases that catalyze galactosylation of an N-acetylgalactosamine linked to a serine or threonine on a protein, polypeptide or peptide have been cloned and expressed.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used as examples for the purpose of description.

Changes may be made in the construction and the operation of the various compositions and elements described herein or in the steps or the sequence of steps of the methods described herein without departing from the spirit and scope of the invention as defined in the following claims.

What is claimed is:

1. An isolated polynucleotide which encodes a protein having core 1 β3-galactosyl transferase activity and which is selected from the group consisting of:

(A) a polynucleotide selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15 AND SEQ ID NO:18;

(B) a polynucleotide which differs in nucleotide sequence from the isolated polynucleotides of (A) above due to degeneracy of the genetic code and which encodes a protein having core 1 β3-galactosyl transferase activity; and (C) a polynucleotide which differs in nucleotide sequence from the polynucleotides of (A) or (B) in that said polynucleotide lacks a nucleotide sequence which encodes a transmembrane domain wherein the core 1 β3-galactosyl transferase encoded is soluble.

2. The polynucleotide of claim 1 wherein the polynucleotide is DNA.

3. A vector containing the polynucleotide of claim 1.

4. A host cell transformed or transfected with the vector of claim 3.

5. A process for producing a purified core 1 β3-galactosyl transferase comprising the steps of:

culturing the host cell of claim 4 thereby expressing the core 1 β3-galactosyl transferase; and purifying the core 1 β3-galactosyl transferase from the cultured host cell.

6. The process of claim 5 wherein the core 1 β3-galactosyl transferase is soluble.

7. The host cell of claim 4 wherein the polynucleotide is operatively associated with an expression control sequence contained in said vector.

8. The host cell of claim 4 transformed or transfected with an expressible polynucleotide encoding a peptide or polypeptide requiring post-translational O-linked glycosylation to form a core 1 structure.

9. The host cell of claim 8 wherein the peptide or polypeptide requiring post-translational O-linked glycosylation to form a core 1 structure comprises P-selectin glycoprotein ligand-1 or a portion thereof which has P-selectin binding activity.

10. A process for producing a purified protein or peptide requiring post translational O-linked glycosylation having a core 1 structure, comprising the steps of:

culturing a host cell having an expressible polynucleotide encoding a peptide or polypeptide requiring post-translational O-linked glycosylation to form a core 1 structure and transformed or transfected with the vector of claim 3;

expressing in the cultured host cell the core 1 β3-galactosyl transferase and the protein or peptide requiring post translational O-linked glycosylation thereby forming a glycosylated protein or peptide having a core 1 structure; and purifying the protein or peptide having a core 1 structure.

* * * * *

SEQUENCE LISTING

<160> NUMBER OF SEQ ID NOS: 25

<210> SEQ ID NO 1
<211> LENGTH: 363

```
<212> TYPE: PRT
<213> ORGANISM: Homo sapiens

<400> SEQUENCE: 1

Met Ala Ser Lys Ser Trp Leu Asn Phe Leu Thr Phe Leu Cys Gly Ser
 1               5                  10                  15

Ala Ile Gly Phe Leu Leu Cys Ser Gln Leu Phe Ser Ile Leu Leu Gly
                20                  25                  30

Glu Lys Val Asp Thr Gln Pro Asn Val Leu His Asn Asp Pro His Ala
            35                  40                  45

Arg His Ser Asp Asp Asn Gly Gln Asn His Leu Glu Gly Gln Met Asn
        50                  55                  60

Phe Asn Ala Asp Ser Ser Gln His Lys Asp Glu Asn Thr Asp Ile Ala
 65                  70                  75                  80

Glu Asn Leu Tyr Gln Lys Val Arg Ile Leu Cys Trp Val Met Thr Gly
                85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
        115                 120                 125

Phe Pro Ala Val Gly Leu Lys Thr Lys Glu Gly Arg Asp Gln Leu Tyr
130                 135                 140

Trp Lys Thr Ile Lys Ala Phe Gln Tyr Val His Glu His Tyr Leu Glu
145                 150                 155                 160

Asp Ala Asp Trp Phe Leu Lys Ala Asp Asp Asp Thr Tyr Val Ile Leu
                165                 170                 175

Asp Asn Leu Arg Trp Leu Leu Ser Lys Tyr Asp Pro Glu Glu Pro Ile
            180                 185                 190

Tyr Phe Gly Arg Arg Phe Lys Pro Tyr Val Lys Gln Gly Tyr Met Ser
        195                 200                 205

Gly Gly Ala Gly Tyr Val Leu Ser Lys Glu Ala Leu Lys Arg Phe Val
    210                 215                 220

Asp Ala Phe Lys Thr Asp Lys Cys Thr His Ser Ser Ser Ile Glu Asp
225                 230                 235                 240

Leu Ala Leu Gly Arg Cys Met Glu Ile Met Asn Val Glu Ala Gly Asp
                245                 250                 255

Ser Arg Asp Thr Ile Gly Lys Glu Thr Phe His Pro Phe Val Pro Glu
            260                 265                 270

His His Leu Ile Lys Gly Tyr Leu Pro Arg Thr Phe Trp Tyr Trp Asn
        275                 280                 285

Tyr Asn Tyr Tyr Pro Pro Val Glu Gly Pro Gly Cys Cys Ser Asp Leu
    290                 295                 300

Ala Val Ser Phe His Tyr Val Asp Ser Thr Thr Met Tyr Glu Leu Glu
305                 310                 315                 320

Tyr Leu Val Tyr His Leu Arg Pro Tyr Gly Tyr Leu Tyr Arg Tyr Gln
                325                 330                 335

Pro Thr Leu Pro Glu Arg Ile Leu Lys Glu Ile Ser Gln Ala Asn Lys
            340                 345                 350

Asn Glu Asp Thr Lys Val Lys Leu Gly Asn Pro
        355                 360     363

<210> SEQ ID NO 2
<211> LENGTH: 1794
<212> TYPE: DNA
<213> ORGANISM: Homo sapiens
```

-continued

```
<400> SEQUENCE: 2
tacagctttg attttataac atcctgctaa ttttgttct tacagaaata cactttcggg      60
aaatggcctc taaatcctgg ctgaattttt taaccttcct ctgtggatca gcaataggat    120
ttcttttatg ttctcagcta tttagtattt tgttgggaga aaaggttgac acccagccta    180
atgttcttca taatgatcct catgcaaggc attcagatga taatggacag atcatctag    240 aaggacaaat gaacttcaat gcagattcta gccaacataa agatgagaac acagacattg    300
ctgaaaacct ctatcagaaa gttagaattc tttgctgggt tatgaccggc cctcaaaacc    360
tagagaaaaa ggccaaacac gtcaaagcta cttgggccca gcgttgtaac aaagtgttgt    420
ttatgagttc agaagaaaat aaagacttcc ctgctgtggg actgaaaacc aaagaaggca    480
gagatcaact atactggaaa acaattaaag cttttcagta tgttcatgaa cattatttag    540
aagatgctga ttggtttttg aaagcagatg atgacacgta tgtcatacta gacaatttga    600
ggtggcttct ttcaaaatac gaccctgaag aacccattta ctttgggaga agatttaagc    660
cttatgtaaa gcagggctac atgagtggag gagcaggata tgtactaagc aaagaagcct    720
tgaaaagatt tgttgatgca tttaaaacag acaagtgtac acatagttcc tccattgaag    780
acttagcact ggggagatgc atggaaatta tgaatgtaga agcaggagat tccagagata    840
ccattggaaa agaaactttt catcccttttg tgccagaaca ccatttaatt aaaggttatc    900
tacctagaac gttttggtac tggaattaca actattatcc tcctgtagag ggtcctggtt    960
gctgctctga tcttgcagtt tcttttcact atgttgattc tacaaccatg tatgagttag   1020
aatacctcgt ttatcatctt cgtccatatg gttatttata cagatatcaa cctaccttac   1080
ctgaacgtat actaaaggaa attagtcaag caaacaaaaa tgaagataca aaagtgaagt   1140
taggaaatcc ttgaaagaaa atcatgaatg aacaaaggta atatgtctag cactgcactg   1200
aaaaaggact tctgcatttc tgacatagaa cactggaatc ccagtgagga attctaagtg   1260
aacattcctt atagaaacct ttcacatgaa tgactataaa ctgaagcttt aaatgagctg   1320
tgaagtgtgt taaatgtgt tttgatacag taatatataa atatgtctat atatatgagg   1380
aacttgtgtt ttttaaatgg tggccaggta gaggaactag aaaagagatt ttgttgcctg   1440
ttttctgacc atctgtgtta ttgtcactga gaaactaaaa tagtaaattt actaaaacta   1500
cactgcacca tgttagtaat aaacagatct gccttaaaga aaagaaaatt ttagaaagaa   1560
atattgttgc tcagtgttgt taatatagct caagaattga gtttatattt gcagtatgct   1620
ataaatgata ccccctacc acaccacac acacagtttt tgtctaatga aatgttgct   1680 gtgattattt ataattggta gtatttcttc cagaagaagc taaataaga ctggcactta   1740 ccctgaagtg cattaataaa accacacttt aaaattaaaa aaaaaaaaaa aaaa          1794
```

```
<210> SEQ ID NO 3
<211> LENGTH: 363
<212> TYPE: PRT
<213> ORGANISM: Rattus norvegicus

<400> SEQUENCE: 3
```

Met Ala Ser Lys Ser Trp Leu Asn Phe Leu Thr Phe Leu Cys Gly Ser
 1               5                  10                  15

Ala Ile Gly Phe Phe Leu Cys Ser Gln Leu Leu Asn Ile Leu Leu Gln
            20                  25                  30

Glu Gln Ala Asp Val Gln Pro Asn Met Leu His Asn Asp Pro His Ala
        35                  40                  45

-continued

```
Arg His Ser Asp Asp Ser Gly His Asn His Leu Lys Gly Gln Met Asp
 50                  55                  60
Phe Asn Ala Asp Ser Ser Gln His Lys Asp Glu Asn Thr Asp Val Ala
 65                  70                  75                  80
Glu Asn Leu Tyr Gln Lys Val Lys Val Leu Cys Trp Val Met Thr Ser
                 85                  90                  95
Pro Gln Asn Leu Glu Lys Lys Ala Lys His Val Lys Ala Thr Trp Ala
                100                 105                 110
Gln Arg Cys Asn Lys Val Leu Phe Met Ser Ser Glu Glu Asn Lys Asp
            115                 120                 125
Phe Pro Thr Val Gly Leu Glu Thr Lys Glu Gly Arg Glu Gln Leu Tyr
        130                 135                 140
Trp Lys Thr Ile Lys Ala Phe Gln Tyr Val His Asp His Tyr Leu Glu
145                 150                 155                 160
Asp Ala Asp Trp Phe Met Lys Ala Asp Asp Thr Tyr Val Ile Leu
                165                 170                 175
Asp Asn Leu Arg Trp Leu Leu Ser Lys Tyr Asn Pro Glu Gln Pro Ile
            180                 185                 190
Tyr Phe Gly Arg Arg Phe Lys Pro Tyr Val Lys Gln Gly Tyr Met Ser
        195                 200                 205
Gly Gly Ala Gly Tyr Val Leu Ser Lys Glu Ala Leu Arg Arg Phe Val
    210                 215                 220
Asp Ala Phe Lys Thr Glu Lys Cys Thr His Ser Ser Ile Glu Asp
225                 230                 235                 240
Leu Ala Leu Gly Arg Cys Met Glu Ile Ile Lys Val Glu Ala Gly Asp
                245                 250                 255
Ser Arg Asp Pro Thr Gly Lys Glu Thr Phe His Pro Phe Val Pro Glu
            260                 265                 270
His His Leu Ile Lys Gly Tyr Leu Pro Lys Thr Phe Trp Tyr Trp Asn
        275                 280                 285
Tyr Asn Tyr Tyr Pro Pro Val Glu Gly Pro Gly Cys Cys Ser Asp Ile
    290                 295                 300
Ala Val Ser Phe His Tyr Val Asp Ser Thr Thr Met Tyr Glu Leu Glu
305                 310                 315                 320
Tyr Leu Val Tyr His Leu Arg Pro Tyr Gly Tyr Leu Tyr Arg Tyr Gln
                325                 330                 335
Pro Ala Leu Pro Glu Asn Ile Leu Lys Glu Ile Asn Gln Val Asn Lys
            340                 345                 350
Lys Glu Asp Thr Lys Ile Lys Leu Gly Asn Pro
        355                 360     363
```

<210> SEQ ID NO 4
<211> LENGTH: 1440
<212> TYPE: DNA
<213> ORGANISM: Rattus norvegicus

<400> SEQUENCE: 4

```
actcaggtgc gggcaccttc cggacgctcc agtccctagt gcctgtggcc gccgctggac    60
cgtcagcttt gtctggagcc ggttgattat ggttgaaact ttccctgccc ttcattgact   120
tgagtgaact gaccagaaat acattcccag gaaatggcct ctaaatcttg gctgaatttt   180
ttaactttcc tctgtggatc agcaatagga ttttcttat gttctcaact cttgaatatt    240
ttgttgcaag aacaggctga cgttcagcct aacatgcttc ataatgatcc tcatgccaga   300
```

-continued

```
cattcagacg acagtggaca taatcacctc aaaggacaga tggacttcaa tgcagattct    360
agccaacata agatgagaa cacagacgtt gctgagaacc tctatcagaa agttaaagtt    420
ctttgttggg ttatgacaag ccctcaaaat ctagagaaaa aggccaaaca cgtcaaagct    480
acatgggccc agcgttgtaa taaagtgtta tttatgagtt cagaagaaaa taaagacttc    540
cctactgtgg ggctggaaac caagaaggc agagagcaac tgtactggaa acaattaaa    600 gcgtttcagt acgtacatga ccattactta gaagatgctg actggtttat gaaagcagac    660
gatgacacct atgtcatact ggacaatctg agatggcttc tatcaaagta taaccctgaa    720
cagcccattt actttgggag aagatttaag ccctatgtga agcagggata catgagtgga    780
ggagcaggat atgtcctaag caaggaagcc ttgagaagat tgtggatgc atttaaaaca    840 gaaaaatgta cgcacagttc ctccattgaa gacttggccc tgggaaggtg catggagatt    900
ataaaggtag aagctgggaga ttccagagat cccactggga aggaaacctt ccaccccttt    960
gtaccagaac accacttaat caaaggctat ctgccaaaaa cattttggta ctggaattac   1020
aactactatc ctcccgtaga gggtcctggt tgctgttctg atattgcagt ttctttttcac   1080 tatgttgatt ctacaactat gtatgaatta gaatacctcg tttatcatct tcgtccatat   1140
ggttatttat atagatatca acctgcctta cctgagaata tactaaaaga aattaatcaa   1200
gtaaacaaaa aggaagatac aaaaataaaa ttaggcaacc cctgaaagca gaccaggagt   1260
ggactgtggt caaatggtct acattgcact gaaggactcc tgcctttgtg acagaacact   1320
gaaatcccag tgaggaactc atctgaagtg gacattccgt atagaaaggt tttcaaatgg   1380
atgactataa actgaagcat ttaaaacctg cccgggccgg ccgctcgagc cctatagtga   1440
```

<210> SEQ ID NO 5
<211> LENGTH: 363
<212> TYPE: PRT
<213> ORGANISM: Mus musculus

<400> SEQUENCE: 5

```
Met Ala Ser Lys Ser Trp Leu Asn Phe Leu Val Phe Leu Cys Gly Ser
 1               5                  10                  15

Ala Ile Gly Phe Phe Leu Cys Ser Gln Leu Leu Ser Ile Leu Leu Arg
                20                  25                  30

Glu Glu Ala Ala Ile Gln Pro Asn Met Leu His Asn Asp Pro His Ala
            35                  40                  45

Arg His Ser Asp Asp Asn Gly His Ser His Leu Lys Gly Gln Met Asn
        50                  55                  60

Phe Asn Ala Asp Ser Ser Gln His Lys Asp Glu Asn Ile Asp Val Ala
 65                  70                  75                  80

Glu Asn Leu Tyr Gln Lys Val Lys Ile Leu Cys Trp Val Met Thr Ser
                85                  90                  95

Pro Gln Asn Leu Glu Lys Lys Ala Lys His Val Lys Ala Thr Trp Ala
                100                 105                 110

Gln Arg Cys Asn Lys Val Leu Phe Met Ser Ser Glu Glu Asn Gln Asp
        115                 120                 125

Phe Pro Thr Val Gly Leu Lys Thr Lys Glu Gly Arg Glu Gln Leu Tyr
    130                 135                 140

Trp Lys Thr Ile Lys Ala Phe Gln Tyr Val His Asp His Tyr Leu Glu
145                 150                 155                 160

Asp Ala Asp Trp Phe Met Lys Ala Asp Asp Thr Tyr Val Ile Val
                165                 170                 175
```

-continued

```
Asp Asn Leu Arg Trp Leu Leu Ser Lys Tyr Asn Pro Glu Gln Pro Ile
            180                 185                 190

Tyr Phe Gly Arg Arg Phe Lys Pro Tyr Val Lys Gln Gly Tyr Met Ser
            195                 200                 205

Gly Gly Ala Gly Tyr Val Leu Ser Lys Glu Ala LeuArg Arg Phe Val
            210                 215                 220

Asn Ala Phe Lys Thr Glu Lys Cys Thr His Ser Ser Ile Glu Asp
225                 230                 235                 240

Leu Ala Leu Gly Arg Cys Met Glu Ile Ile Asn Val Glu Ala Gly Asp
                245                 250                 255

Ser Arg Asp Thr Ile Gly Lys Glu Thr Phe His Pro Phe Val Pro Glu
            260                 265                 270

His His Leu Ile Lys Gly Tyr Leu Pro Lys Thr Phe Trp Tyr Trp Asn
            275                 280                 285

Tyr Asn Tyr Tyr Pro Pro Ile Glu Gly Pro Gly Cys Cys Ser Asp Ile
            290                 295                 300

Ala Val Ser Phe His Tyr Val Asp Gly Thr Thr Met Tyr Glu Leu Glu
305                 310                 315                 320

Tyr Leu Val Tyr His Leu Arg Pro Tyr Gly Tyr Leu Tyr Arg Tyr Gln
                325                 330                 335

Pro Ala Leu Pro Glu Asn Ile Leu Lys Glu Ile Asn Gln Val Asn Arg
            340                 345                 350

Lys Glu Asp Thr Lys Ile Lys Leu Gly Asn Pro
            355                 360        363

<210> SEQ ID NO 6
<211> LENGTH: 1469
<212> TYPE: DNA
<213> ORGANISM: Mus musculus

<400> SEQUENCE: 6
ggcttgggct cgagcggccg cccgggcagg tctcaggtgc cggcaccttc cggccgcaac     60
agtcccgagt gccgccgcc gttgaccgt cagctttgtc tggagctggt cggttatggt     120
tggaactttc cctgcccttc gttgactgag tgaaccagcc agaaatacat tcccaggaaa    180
tggcctctaa atcttggctg aattttttag tcttcctctg tggatcagca atagggtttt    240
ttttatgttc tcaactcttg agtattttgt tgcgagaaga ggctgccatt cagcctaaca    300
tgcttcacaa tgaccctcat gcaaggcatt cagatgacaa tggacacagt cacctcaaag    360
gacagatgaa cttcaatgca gattccagcc aacataaaga tgagaacata gacgttgctg    420
agaacctcta tcagaaagtt aaaattcttt gttgggttat gacaagtcct caaaatctag    480
agaaaaaggc caaacatgtc aaagctacgt gggcccagcg ttgtaataaa gtgttattta    540
tgagttcgga agaaaatcaa gacttcccta ctgtgggatt gaaaaccaaa gaaggcagag    600
agcaactata ttgaaaaaca attaaagctt tccagtatgt acatgaccat tatttagaag    660
atgctgactg gtttatgaaa gcagatgacg acacatacgt cattgtggac aacctgagat    720
ggcttctatc aaagtataac ctgaacaac ccatttactt tgggcgaaga tttaagccct    780
atgtgaagca gggatacatg agcggaggag cgggctatgt cctaagcaag gaagccttga    840
gaagatttgt taatgcattt aaaacagaaa agtgtacaca tagttcctcc atcgaagact    900
tagctctggg aaggtgcatg gaattataa atgtagaagc tggagattcc agagatacca    960
ttgggaaaga aaccttccat ccatttgtac cagaacacca cttaatcaaa ggttatctac   1020
caaaaacatt tggtactgg aattacaact attatcctcc catagagggt cctggatgct   1080
```

-continued

```
gttctgatat cgcagtttct tttcactatg ttgatgggac aactatgtat gaattagaat   1140
acctcgttta tcatcttcgt ccatatggtt atttatatag atatcaacct gccttacctg   1200
agaatatact gaaagaaatt aatcaagtaa acagaaagga agatacaaaa ataaaattag   1260
gcaacccctg aaagcagaac ataagtggtc tacattgcac tgaaggactc ttgcctttct   1320
acggaaccct gaaatcccag tgaggaactc acctgaagtg aacattccat atagaaatct   1380
ttcaaatgga tgactataaa ctgaagcatt taaagagctg tgaagtttgc taaaacgtgt   1440
tttgatacag taatatataa atataaata                                     1469
```

<210> SEQ ID NO 7
<211> LENGTH: 389
<212> TYPE: PRT
<213> ORGANISM: Caenorhabditis elegans

<400> SEQUENCE: 7

```
Met Ala Asn Trp Pro Arg Val Ser Pro Leu Ala Tyr Val Ala Leu Gly
  1               5                  10                  15

Val Leu Leu Gly Leu Thr Ile Ser Ile Ser Gln Thr Gly Thr Thr
                 20                  25                  30

Thr Tyr Asp Ala Ala Ser Arg Ile Ala Ile Leu Arg Ala Asn Arg Gly
             35                  40                  45

Asp Pro Gln Val Asp Glu His Asp Ala His Gly Asn Asp Pro His
         50                  55                  60

Gly Asp Glu Glu Val Asp Asp His His Ala Asn Phe Ala Pro Val Gln
 65                  70                  75                  80

Phe His Ser Asn Asn Ser Ser Ser His Asp Gly Glu Ser Leu Ile
                 85                  90                  95

Ala Lys Lys Val Arg Val Phe Cys Trp Ile Leu Thr Gly Lys Gln Asn
            105                 110                 115

His Asp Lys Arg Ala Lys His Val Lys Ala Thr Trp Ala Lys Arg Cys
            120                 125                 130

Asn Lys Tyr Val Phe Met Ser Ser Glu Glu Asp Ala Glu Leu Pro Ala
            135                 140                 145

Ile Asn Leu Asn Val Ser Glu Gly Arg Asp Tyr Leu Trp Ala Lys Thr
150                 155                 160

Lys Gly Ala Phe Lys Tyr Ile Tyr Asp His His Leu Asn Asp Tyr Asp
165                 170                 175                 180

Trp Phe Leu Lys Ala Asp Asp Thr Tyr Val Val Met Glu Asn Leu
                185                 190                 195

Arg Phe Met Leu Leu Ala His Ser Pro Asp Glu Pro Ile His Phe Gly
                200                 205                 210

Cys Lys Phe Lys Pro Phe Thr Gln Gly Gly Tyr His Ser Gly Gly Ala
            215                 220                 225

Gly Tyr Val Leu Ser Arg Glu Ala Leu Lys Lys PheIle Glu Val Ala
            230                 235                 240

Leu Pro Asp Lys Ser Leu Cys Ser Gln Asn His Gly Gly Ala Glu Asp
245                 250                 255                 260

Ala Glu Met Gly Lys Cys Leu Glu Lys Val Gly Val Lys Ala Gly Asp
                265                 270                 275

Ser Arg Asp Ala Asp Gly His His Arg Phe Met Pro Phe Val Pro Glu
            280                 285                 290

His His Leu Ser Pro Gly His Val Asp Pro Lys Phe Trp Phe Trp Gln
            295                 300                 305
```

```
Tyr Thr Tyr Tyr Pro Met Asp Gln Gly Pro Thr Cys Cys Ser Asp Tyr
        310                 315                 320

Ala Val Ser Phe His Tyr Val Asn Pro Asn Leu Met Tyr Val Leu Glu
325                 330                 335                 340

Tyr Leu Ile Tyr His Leu Lys Pro Phe Gly Ile Asp Arg Ala Ile Arg
                345                 350                 355

Val Pro Lys Asn Glu Thr Ile Ile His Thr Ala Tyr Ser Ile Ser Arg
                360                 365                 370

Ser Glu Arg Gly Gln Asp Asp Ala Phe Arg Asp Arg Pro Glu Val Ala
            375                 380                 385

Val
389

<210> SEQ ID NO 8
<211> LENGTH: 1172
<212> TYPE: DNA
<213> ORGANISM: Caenorhabditis elegans

<400> SEQUENCE: 8
atggcaaact ggccacgtgt tctcctctc gcctacgtgg cgcttggcgt tcttctcggt      60
ttgaccattt caataatatc tcagacggga acgacaacct acgacgctgc ctcacggata    120
gccatactac gagccaaccg aggggatcca caagttgacg agcacgatca tgcacatgga    180
aatgatccgc acgagacga agaagtcgac gatcatcacg gaactttgc gcccgtccaa      240 ttccattcca caactcatc gcatagccat gatggtgaaa gtctgatagc cgacgaagtt    300
gcgaagaagg ttcgcgtctt ctgttggatt ctcaccggaa acagaatca cgataaacgc    360 gcgaaacacg tcaaagccac ctgggccaag cggtgtaata agtacgtatt catgtcatca    420
gaagaggatg cagaactccc agccatcaac ctaaatgtct ctgaaggcag agattacttg    480
tgggcaaaaa caaaggagc attcaaatac atttatgacc atcacctgaa cgactacgac    540
tggttcctga agccgacga cgataccta tgtggtgatgg aaaatctccg gttcatgcta    600
ttggctcatt caccggatga gccaattcac tttggatgca gtttaagcc attcacacag    660 ggaggatatc atagtggtgg agctggatat gtgctcagtc gggaggcact gaaaaaattc    720
attgaagtag cgctgccgga caaatcgttg tgctctcaga tcatggtgg agccgaggat    780 gcggagatgg gcaaatgctt ggagaaggtt ggagtgaaag ctggagattc agagatgcc     840 gatggacatc atagattcat gcctttcgtg ccggaacatc acttgtcgcc tggccacgtt    900
gaccccaagt tctggttctg gcagtacact tactacccaa tggatcaagg acctacgtgt    960
tgctctgatt acgcagtctc cttccactac gtcaaccga acttgatgta tgtgctcgag   1020
tatctcatct atcacttgaa gcctttcggt atcgatcgcg cgattcgagt gccaagaac    1080 gaaacaataa tccatacggc ttattccatc tctcgatccg aacgtggaca agacgatgcg   1140
ttccgggatc ggccggaagt tgctgtataa gc                                 1172

<210> SEQ ID NO 9
<211> LENGTH: 367
<212> TYPE: PRT
<213> ORGANISM: Drosophila melanogaster

<400> SEQUENCE: 9

Met Thr Ser Ala Ser Leu Leu Ser Arg Ser Leu Leu Thr Glu Ala Pro
  1               5                  10                  15

Arg Ser Lys Asn Arg Ser Val Phe Thr Leu Ile Ala Gly Leu Val Val
```

```
                   20                  25                  30
Gly Tyr Cys Leu Ala Gln Ile Phe Ser Ser Ile Ala Pro His Glu Ser
             35                  40                  45
Leu Tyr Pro Tyr Leu Ser Arg Arg Phe Ser Asp Ser Gln Val Ala Thr
         50                  55                  60
Gly Gly Gln Leu Ala Pro Glu Gln Ser Gly Leu Lys His Asp His Arg
 65                  70                  75                  80
Asn Asp Asn Val Ser Val Ala Glu Gln Leu Lys Lys Glu Val Arg Ile
                 85                  90                  95
Leu Cys Trp Val Met Thr Asn Pro Thr Asn His Lys Lys Ala Arg
            100                 105                 110
His Val Lys Arg Thr Trp Gly Lys Arg Cys Asn Ile Leu Leu Phe Met
        115                 120                 125
Ser Ser Gly Ala Asp Glu Glu Leu Pro Thr Val Lys Leu Asp Val Gly
130                 135                 140
Glu Gly Arg Glu Asn Leu Trp Ala Lys Val Lys Glu Ala Phe Lys Tyr
145                 150                 155                 160
Val Tyr His His His Tyr Asn Asp Ala Asp Phe Phe Tyr Lys Ala Asp
                165                 170                 175
Asp Asp Thr Tyr Ala Val Ile Glu Asn Met Arg Tyr Met Leu Tyr Pro
            180                 185                 190
Tyr Asn Pro Glu Thr Pro Val His Phe Gly Phe Lys Phe Lys Pro Phe
        195                 200                 205
Val Lys Gln Gly Tyr Met Ser Gly Gly Ala Gly Tyr Ile Leu Ser Arg
    210                 215                 220
Glu Ala Leu Arg Arg Phe Val Val Glu Gly Ile Pro Asn Pro Lys Met
225                 230                 235                 240
Cys Leu Pro Gly Thr Val Val Asn Glu Asp Ile Glu Ile Gly Arg Cys
                245                 250                 255
Met Glu Asn Leu Asn Val Thr Ala Gly Asp Ser Arg Asp Glu Ile Gly
            260                 265                 270
Arg Gly Arg Met Phe Pro Phe Ile Pro Glu His His Leu Ile Pro Ala
        275                 280                 285
Lys Ala Asp Lys Asn Phe Trp Tyr Trp Asn Tyr Leu Tyr Tyr Lys Thr
    290                 295                 300
Asp Asp Gly Leu Asp Cys Cys Ser Asp Leu Ala Ile Ser Phe His Tyr
305                 310                 315                 320
Val Ala Pro Asn Ser Phe Tyr Val Leu Asp Tyr Leu Ile Tyr His Leu
                325                 330                 335
Lys Pro Tyr Gly Leu Leu Arg Ser Leu Glu Pro Leu Pro Ala Lys Leu
            340                 345                 350
Lys Val Gly Gln Phe Leu Pro Pro Glu Thr Ser Lys Glu Asn
        355                 360                 365 367

<210> SEQ ID NO 10
<211> LENGTH: 1104
<212> TYPE: DNA
<213> ORGANISM: Drosophila melanogaster

<400> SEQUENCE: 10
atgacgagtg caagtctatt gtcgcgttcc ctgctaacag aagctccgcg ttctaagaat    60
cgctcggtgt ttaccttgat tgctggtttg gtggtcggct actgcctggc tcaaatcttc   120
tccagcattg cgccgcacga gagtctctat ccgtatctca gcagacggtt cagcgattcc   180
```

```
caggtggcca ccggtggtca attggctccg gagcagagcg ggttgaagca tgatcatcgc    240
aacgacaacg tcagcgtggc cgagcagttg aagaaggagg tacgcatcct ctgctgggtg    300
atgaccaatc ccacaaacca caagaagaag gctcgccatg tgaagcgaac ctggggcaag    360
cgctgcaaca tcttgctctt catgagttcc ggcgcggatg aggagctgcc caccgtgaag    420
ctcgacgtgg gcgagggacg ggagaatcta tgggccaagg tcaaggaggc gttcaagtac    480
gtctatcatc accactataa cgacgccgac ttcttctaca aggccgatga cgacacttac    540
gccgtgatcg agaacatgcg gtatatgctc tatccgtaca atcccgaaac acccgtgcac    600
ttcggattca agttcaagcc cttcgtgaag cagggctaca tgtccggcgg agcgggctac    660
atactcagtc gggaggccct gcgtcgcttc gtggtcgagg gcattccgaa tcccaagatg    720
tgcctgccgg gcacggtggt caacgaggac atcgaaatcg gcgatgcat  ggagaacctg    780 aacgtcaccg ccggcgattc cagggacgaa atcggtcgcg gtcgcatgtt ccccttcata    840
ccggagcatc acttgatccc agccaaggcg gataaaaact tttggtactg gaactacctt    900
tactacaaga cggatgacgg tctcgactgc tgctcggact tggccatctc ctttcactac    960
gtagctccga attccttcta tgtcctggac tatctcatct accacttgaa acccctacggc   1020 ctactgcgat ccctggagcc tctgcccgcc aaactcaaag tgggtcagtt tctgccgcct   1080
cccgaaacat cgaaagaaaa ttaa                                          1104
```

<210> SEQ ID NO 11
<211> LENGTH: 350
<212> TYPE: PRT
<213> ORGANISM: Homo sapiens

<400> SEQUENCE: 11

```
Met Arg Leu Ala Val Gly Ala Leu Leu Val Cys Ala Val Leu Gly Leu
 1               5                  10                  15

Cys Leu Ala Glu Asp Gln Val Asp Pro Arg Leu Ile Asp Gly Lys Asp
                20                  25                  30

Pro His Ala Arg His Ser Asp Asp Asn Gly Gln Asn His Leu Glu Gly
            35                  40                  45

Gln Met Asn Phe Asn Ala Asp Ser Ser Gln His Lys Asp Glu Asn Thr
        50                  55                  60

Asp Ile Ala Glu Asn Leu Tyr Gln Lys Val Arg Ile Leu Cys Trp Val
65                  70                  75                  80

Met Thr Gly Pro Gln Asn Leu Glu Lys Lys Ala Lys His Val Lys Ala
                85                  90                  95

Thr Trp Ala Gln Arg Cys Asn Lys Val Leu Phe Met Ser Ser Glu Glu
            100                 105                 110

Asn Lys Asp Phe Pro Ala Val Gly Leu Lys Thr Lys Glu Gly Arg Asp
        115                 120                 125

Gln Leu Tyr Trp Lys Thr Ile Lys Ala Phe Gln Tyr Val His Glu His
    130                 135                 140

Tyr Leu Glu Asp Ala Asp Trp Phe Leu Lys Ala Asp Asp Asp Thr Tyr
145                 150                 155                 160

Tyr Trp Asn Tyr Asn Tyr Tyr Pro Val Ile Leu Asp Asn Leu Arg Trp
            275                 280                 165

Leu Leu Ser Lys Tyr Asp Pro Glu Glu Pro Ile Tyr Phe Gly Arg Arg
        170                 175                 180

Phe Lys Pro Tyr Val Lys Gln Gly Tyr Met Ser Gly Gly Ala Gly Tyr
    185                 190                 195                 200
```

-continued

```
Val Leu Ser Lys Glu Ala Leu Lys Arg Phe Val Asp Ala Phe Lys Thr
            205                 210                 215
Asp Lys Cys Thr His Ser Ser Ile Glu Asp Leu Ala Leu Gly Arg
        220                 225                 230
Cys Met Glu Ile Met Asn Val Glu Ala Gly Asp Ser Arg Asp Thr Ile
            235                 240                 245
Gly Lys Glu Thr Phe His Pro Phe Val Pro Glu His His Leu Ile Lys
        250                 255                 260
Gly Tyr Leu Pro Arg Thr Phe Trp Pro Val Glu Gly Pro Gly Cys Cys
265                 270                             285
Ser Asp Leu Ala Val Ser Phe His Tyr Val Asp Ser Thr Thr Met Tyr
        290                 295                 300
Glu Leu Glu Tyr Leu Val Tyr His Leu Arg Pro Tyr Gly Tyr Leu Tyr
305                 310                 315                 320
Arg Tyr Gln Pro Thr Leu Pro Glu Arg Ile Leu Lys Glu Ile Ser Gln
                325                 330                 335
Ala Asn Lys Asn Glu Asp Thr Lys Val Lys Leu Gly Asn Pro
            340                 345                 350
```

<210> SEQ ID NO 12
<211> LENGTH: 1092
<212> TYPE: DNA
<213> ORGANISM: Homo sapiens

<400> SEQUENCE: 12

```
atggcctcta aatcctggct gaattttta  accttcctct gtggatcagc aataggattt     60
cttttatgtt ctcagctatt tagtattttg ttgggagaaa aggttgacac ccagcctaat    120
gttcttcata tgatcctca  tgcaaggcat tcagatgata atggacagaa tcatctagaa    180
ggacaaatga acttcaatgc agattctagc aacataaag  atgagaacac agacattgct    240
gaaaacctct atcagaaagt tagaattctt tgctggggta tgaccggccc tcaaaaccta    300
gagaaaaagg ccaaacacgt caaagctact tgggcccagc gttgtaacaa agtgttgttt    360
atgagttcag aagaaaataa agacttccct gctgtgggac tgaaaaccaa agaaggcaga    420
gatcaactat actggaaaac aattaaagct tttcagtatg ttcatgaaca ttatttagaa    480
gatgctgatt ggttttttgaa agcagatgat gacacgtatg tcatactaga caatttgagg    540
tggcttcttt caaaatacga ccctgaagaa cccatttact tgggagaag  atttaagcct    600
tatgtaaagc agggctacat gagtggagga gcaggatatg tactaagcaa agaagccttg    660
aaaagatttg ttgatgcatt taaaacagac aagtgtacac atagttcctc cattgaagac    720
ttagcactgg ggagatgcat ggaaattatg aatgtagaag caggagattc cagagatacc    780
attggaaaag aaactttca  tcccttgtg  ccagaacacc atttaattaa aggttatcta    840
cctagaacgt tttggtactg gaattacaac tattatcctc ctgtagaggg tcctggttgc    900
tgctctgatc ttgcagttc  ttttcactat gttgattcta caaccatgta tgagttagaa    960
tacctcgttt atcatcttcg tccatatggt tatttataca gatatcaacc taccttacct   1020
gaacgtatac taaaggaaat tagtcaagca aacaaaatg  aagatacaaa agtgaagtta   1080
ggaaatcctt ga                                                       1092
```

<210> SEQ ID NO 13
<211> LENGTH: 1092
<212> TYPE: DNA
<213> ORGANISM: Rattus norvegicus

<400> SEQUENCE: 13

| | |
|---|---|
| atggcctcta aatcttggct gaattttta actttcctct gtggatcagc aataggattt | 60 |
| ttcttatgtt ctcaactctt gaatattttg ttgcaagaac aggctgacgt tcagcctaac | 120 |
| atgcttcata atgatcctca tgccagacat tcagacgaca gtggacataa tcacctcaaa | 180 |
| ggacagatgg acttcaatgc agattctagc aacataaag atgagaacac agacgttgct | 240 |
| gagaacctct atcagaaagt taaagttctt tgttgggtta tgacaagccc tcaaaatcta | 300 |
| gagaaaaagg ccaaacacgt caaagctaca tgggcccagc gttgtaataa agtgttattt | 360 |
| atgagttcag aagaaaataa agacttccct actgtggggc tggaaaccaa agaaggcaga | 420 |
| gagcaactgt actggaaaac aattaaagcg tttcagtacg tacatgacca ttacttagaa | 480 |
| gatgctgact ggtttatgaa agcagacgat gacacctatg tcatactgga caatctgaga | 540 |
| tggcttctat caaagtataa ccctgaacag cccatttact ttgggagaag atttaagccc | 600 |
| tatgtgaagc agggatacat gagtggagga gcaggatatg tcctaagcaa ggaagccttg | 660 |
| agaagatttg tggatgcatt taaaacagaa aaatgtacgc acagttcctc cattgaagac | 720 |
| ttggccctgg aaggtgcat ggagattata aggtagaag ctggagattc cagagatccc | 780 |
| actgggaagg aaaccttcca ccctttgta ccagaacacc acttaatcaa aggctatctg | 840 |
| ccaaaaacat tttggtactg gaattacaac tactatcctc ccgtagaggg tcctggttgc | 900 |
| tgttctgata ttgcagtttc ttttcactat gttgattcta caactatgta tgaattagaa | 960 |
| tacctcgttt atcatcttcg tccatatggt tatttatata gatatcaacc tgccttacct | 1020 |
| gagaatatac taaagaaat taatcaagta aacaaaagg aagatacaaa ataaaatta | 1080 |
| ggcaaccct ga | 1092 |

<210> SEQ ID NO 14
<211> LENGTH: 1092
<212> TYPE: DNA
<213> ORGANISM: Mus musculus

<400> SEQUENCE: 14

| | |
|---|---|
| atggcctcta aatcttggct gaattttta gtcttcctct gtggatcagc aatagggttt | 60 |
| ttttatgtt ctcaactctt gagtattttg ttgcgagaag aggctgccat tcagcctaac | 120 |
| atgcttcaca atgaccctca tgcaaggcat tcagatgaca atggacacag tcacctcaaa | 180 |
| ggacagatga acttcaatgc agattccagc aacataaag atgagaacat agacgttgct | 240 |
| gagaacctct atcagaaagt taaaattctt tgttgggtta tgacaagtcc tcaaaatcta | 300 |
| gagaaaaagg ccaaacatgt caaagctacg tgggcccagc gttgtaataa agtgttattt | 360 |
| atgagttcgg aagaaaatca agacttccct actgtgggat tgaaaccaa agaaggcaga | 420 |
| gagcaactat attggaaaac aattaaagct ttccagtatg tacatgacca ttatttagaa | 480 |
| gatgctgact ggtttatgaa agcagatgac gacacatacg tcattgtgga caacctgaga | 540 |
| tggcttctat caaagtataa ccctgaacaa cccatttact ttgggcgaag atttaagccc | 600 |
| tatgtgaagc agggatacat gagcggagga gcgggctatg tcctaagcaa ggaagccttg | 660 |
| agaagatttg ttaatgcatt taaaacagaa aagtgtacac atagttcctc catcgaagac | 720 |
| ttagctctgg aaggtgcat ggaaattata atgtagaag ctggagattc cagagatacc | 780 |
| attgggaaag aaaccttcca tccatttgta ccagaacacc acttaatcaa aggttatcta | 840 |
| ccaaaaacat tttggtactg gaattacaac tattatcctc ccatagaggg tcctggatgc | 900 |
| tgttctgata tcgcagtttc ttttcactat gttgatggga caactatgta tgaattagaa | 960 |

```
tacctcgttt atcatcttcg tccatatggt tatttatata gatatcaacc tgccttacct    1020
gagaatatac tgaaagaaat taatcaagta aacagaaagg aagatacaaa aataaaatta    1080
ggcaacccct ga                                                        1092

<210> SEQ ID NO 15
<211> LENGTH: 1170
<212> TYPE: DNA
<213> ORGANISM: Caenorhabditis  elegans

<400> SEQUENCE: 15
atggcaaact ggccacgtgt ttctcctctc gcctacgtgg cgcttggcgt tcttctcggt      60
ttgaccattt caataatatc tcagacggga acgacaacct acgacgctgc ctcacggata     120
gccatactac gagccaaccg agggatcca caagttgacg agcacgatca tgcacatgga     180
aatgatccgc acgagacga agaagtcgac gatcatcacg cgaactttgc gcccgtccaa     240
ttccattcca acaactcatc gcatagccat gatggtgaaa gtctgatagc cgacgaagtt     300
gcgaagaagg ttcgcgtctt ctgttggatt ctcaccggaa acagaatca cgataaacgc     360 gcgaaacacg tcaaagccac ctgggccaag cggtgtaata agtacgtatt catgtcatca     420
gaagaggatg cagaactccc agccatcaac ctaaatgtct ctgaaggcag agattacttg     480
tgggcaaaaa caaaggagc attcaaatac atttatgacc atcacctgaa cgactacgac     540
tggttcctga agccgacga cgatacctat gtggtgatgg aaaatctccg gttcatgcta     600
ttggctcatt caccggatga gccaattcac tttggatgca agtttaagcc attcacacag     660
ggaggatatc atagtggtgg agctggatat gtgctcagtc gggaggcact gaaaaaattc     720
attgaagtag cgctgccgga caaatcgttg tgctctcaga tcatggtgg agccgaggat     780 gcggagatgg gcaaatgctt ggagaaggtt ggagtgaaag ctggagattc cagagatgcc     840
gatggacatc atagattcat gcctttcgtg ccggaacatc acttgtcgcc tggccacgtt     900
gaccccaagt tctggttctg gcagtacact tactacccaa tggatcaagg acctacgtgt     960
tgctctgatt acgcagtctc cttccactac gtcaacccga acttgatgta tgtgctcgag    1020
tatctcatct atcacttgaa gcctttcggt atcgatcgcg cgattcgagt gccaaagaac    1080
gaaacaataa tccatacggc ttattccatc tctcgatccg aacgtggaca agacgatgcg    1140
ttccgggatc ggccggaagt tgctgtataa                                     1170

<210> SEQ ID NO 16
<211> LENGTH: 28
<212> TYPE: PRT
<213> ORGANISM: Homo sapiens

<400> SEQUENCE: 16

Ser Trp Leu Asn Phe Leu Thr Phe Leu Cys Gly Ser Ala Ile Gly Phe
  1               5                  10                  15

Leu Leu Cys SerGln Leu Phe Ser Ile Leu Leu Gly
             20                  25          28

<210> SEQ ID NO 17
<211> LENGTH: 388
<212> TYPE: PRT
<213> ORGANISM: Drosophila melanogaster

<400> SEQUENCE: 17

Met Thr Ala Asn Ser Leu Leu Gly Arg Ser Ile Leu Asn Glu Gly Arg
  1               5                  10                  15
```

-continued

```
Ser Asn Lys Arg Ser Phe Val Ser Leu Ile Val Gly Leu Ile Val Gly
             20                  25                  30

Phe Cys Leu Ala Glu Leu Phe Val Tyr Ser Thr Pro Glu Arg Ser Glu
             35                  40                  45

Phe Met Pro Tyr Asp Gly His Arg His Gly Asp Val Asn Asp Ala His
             50                  55                  60

His Ser His Asp Met Met Glu Met Ser Gly Pro Glu Gln Asp Val Gly
 65                  70                  75                  80

Gly His Glu His Val His Glu Asn Ser Thr Ile Ala Glu Arg Leu Tyr
                     85                  90                  95

Ser Glu Val Arg Val Leu Cys Trp Ile Met Thr Asn Pro Ser Asn His
            100                 105                 110

Gln Lys Lys Ala Arg His Val Lys Arg Thr Trp Gly Lys Arg Cys Asn
            115                 120                 125

Lys Leu Ile Phe Met Ser Ser Ala Lys Asp Asp Glu Leu Asp Ala Val
            130                 135                 140

Ala Leu Pro Val Gly Glu Gly Arg Asn Asn Leu Trp Gly Lys Thr Lys
145                 150                 155                 160

Glu Ala Tyr Lys Tyr Ile Tyr Glu His His Ile Gln Asp Ala Asp Trp
                165                 170                 175

Phe Leu Lys Ala Asp Asp Asp Thr Tyr Thr Ile Val Glu Asn Met Arg
            180                 185                 190

Tyr Met Leu Tyr Pro Tyr Ser ProGlu Thr Pro Val Tyr Phe Gly Cys
            195                 200                 205

Lys Phe Lys Pro Tyr Val Lys Gln Gly Tyr Met Ser Gly Gly Ala Gly
            210                 215                 220

Tyr Val Leu Ser Arg Glu Ala Val Arg Arg Phe Val Val Glu Ala Leu
225                 230                 235                 240

Pro Asn Pro Lys Leu Cys Lys Ser Asp Asn Ser Gly Ala Glu Asp Val
                245                 250                 255

Glu Ile Gly Lys Cys Leu Gln Asn Val Asn Val Leu Ala Gly Asp Ser
            260                 265                 270

Arg Asp Ser Asn Gly Arg Gly Arg Phe Phe Pro Phe Val Pro Glu His
            275                 280                 285

His Leu Ile Pro Ser His Thr Asp Lys Lys Phe Trp Tyr Trp Gln Tyr
            290                 295                 300

Ile Phe Tyr Lys Thr Asp Glu Gly Leu Asp Cys Cys Ser Asp Asn Ala
305                 310                 315                 320

Ile Ser Phe His Tyr Val Ser Pro Asn Gln Met Tyr Val Leu Asp Tyr
                325                 330                 335

Leu Ile Tyr His Leu Arg Pro Tyr Gly Ile Ile Asn Thr Pro Asp Ala
            340                 345                 350

Leu Pro Asn Lys Leu Ala Val Gly Glu Leu Met Pro Glu Ile Lys Glu
            355                 360                 365

Gln Ala Thr Glu Ser Thr Ser Asp Gly Val Ser Lys Arg Ser Ala Glu
            370                 375                 380

Thr Lys Thr Gln
385         388

<210> SEQ ID NO 18
<211> LENGTH: 1167
<212> TYPE: DNA
<213> ORGANISM: Drosophila melanogaster
```

<400> SEQUENCE: 18

```
atgactgcca acagtctgct aggaaggtcc atactcaatg aaggtcgctc aaacaagcga    60
tcatttgtgt ccctgattgt gggcctgatc gtgggcttct gcctggcgga gctgttcgtc   120
tactccacgc cggagcgaag tgaattcatg ccatacgatg ccatcggca cggcgacgtg    180
aacgatgcac atcacagcca cgacatgatg gagatgtccg gaccggaaca ggacgtgggt   240
ggacacgagc acgtgcacga gaactcgacc attgcggagc gactgtacag cgaggtgcgt   300
gtgctctgct ggatcatgac caatccgagc aaccatcaga agaaggcgcg ccacgtgaag   360
cgcacctggg gcaagcgttg caacaagctg atctttatga gctccgccaa ggacgacgag   420
ctggacgcag tggctctgcc cgtaggcgag ggtcgcaaca acctatgggg caagacgaag   480
gaggcctaca atacatcta cgagcatcac atcaacgacg ccgactggtt cctgaaggct   540
gacgatgaca catacacgat agtggagaac atgcgataca tgctgtatcc gtacagtccg   600
gaaactccag tctacttcgg ctgcaagttc aagccgtacg tgaaacaagg ctacatgtcc   660
ggcggtgccg gctacgttct cagccgggag gctgtgcgtc gctttgtggt cgaagccctg   720
cccaatccga agctgtgcaa gtcggataac tcgggtgctg aggacgtgga gattggcaaa   780
tgtctgcaga atgtaaacgt gctcgctggg gactcgcgag actcaaacgg tcggggtcgc   840
ttctttccat ttgtgcccga gcaccatctg attccatcgc acacggacaa gaagttctgg   900
tactggcagt atatcttcta caagacggat gagggacttg actgctgctc ggacaacgcc   960
atatcgttcc actacgtctc ccccaatcaa atgtatgtgc tggattatct gatctaccat  1020
ctgagaccgt acgggatcat aaacacaccc gatgcgttgc cgaataagct agccgtgggc  1080
gaactgatgc cggagatcaa ggagcaggcg acggaaagca caagtgatgg ggtctccaag  1140
agatccgccg agacaaagac gcaataa                                      1167
```

<210> SEQ ID NO 19
<211> LENGTH: 29
<212> TYPE: DNA
<213> ORGANISM: Homo sapiens

<400> SEQUENCE: 19

```
gatccaccat ggcctctaaa tcctggctg                                      29
```

<210> SEQ ID NO 20
<211> LENGTH: 29
<212> TYPE: DNA
<213> ORGANISM: Homo sapiens

<400> SEQUENCE: 20

```
aattcagcca ggatttagag gccatggtg                                      29
```

<210> SEQ ID NO 21
<211> LENGTH: 15
<212> TYPE: DNA
<213> ORGANISM: Homo sapiens

<400> SEQUENCE: 21

```
gatcctcatg caagg                                                     15
```

<210> SEQ ID NO 22
<211> LENGTH: 9
<212> TYPE: DNA
<213> ORGANISM: Homo sapiens

<400> SEQUENCE: 22

```
ttgcatgag                                                                9

<210> SEQ ID NO 23
<211> LENGTH: 22
<212> TYPE: DNA
<213> ORGANISM: Homo sapiens

<400> SEQUENCE: 23
ctttatgttg gctagaatct gc                                                22

<210> SEQ ID NO 24
<211> LENGTH: 19
<212> TYPE: PRT
<213> ORGANISM: Homo sapiens

<400> SEQUENCE: 24

Met Arg Leu Ala Val Gly Ala Leu Leu Val Cys Ala Val Leu Gly Leu
  1               5                  10                  15

Cys Leu Ala
         19

<210> SEQ ID NO 25
<211> LENGTH: 12
<212> TYPE: PRT
<213> ORGANISM: Homo sapiens

<400> SEQUENCE: 25

Glu Asp Gln Val Asp Pro Arg Leu Ile Asp Asp Lys
  1               5                  10      12
```